(12) United States Patent
Peuker et al.

(10) Patent No.: US 9,283,060 B2
(45) Date of Patent: Mar. 15, 2016

(54) DEVICE FOR DISPENSING A DENTAL SUBSTANCE AND METHOD OF DISPENSING

(75) Inventors: Marc Peuker, Schondorf (DE); Helmut Pauser, Diessen (DE); Mathias Bertl, Wildsteig (DE); Olaf Althoff, Wessling (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/235,139

(22) PCT Filed: Jul. 27, 2012

(86) PCT No.: PCT/US2012/048561
§ 371 (c)(1),
(2), (4) Date: Jan. 29, 2014

(87) PCT Pub. No.: WO2013/016642
PCT Pub. Date: Jan. 31, 2013

(65) Prior Publication Data
US 2014/0197195 A1    Jul. 17, 2014

(30) Foreign Application Priority Data

Jul. 28, 2011   (EP) .................................... 11175728

(51) Int. Cl.
*B67D 1/00*      (2006.01)
*A61C 9/00*      (2006.01)
(Continued)

(52) U.S. Cl.
CPC ............ *A61C 9/0026* (2013.01); *B05C 17/0052* (2013.01); *B05C 17/00576* (2013.01); *B05C 17/0116* (2013.01); *B05C 17/0133* (2013.01); *B65D 81/325* (2013.01); *B65D 83/0016* (2013.01); *B05C 17/00583* (2013.01)

(58) Field of Classification Search
CPC ............. A61C 9/0026; B05C 17/0052; B05C 17/00576; B05C 17/0016; B05C 17/0133; B05C 17/00583; B65D 81/325; B65D 83/0016
USPC .......... 222/39, 80, 144.5, 390, 136, 137, 326, 222/327, 469, 549, 553; 433/89, 144
See application file for complete search history.

(56) References Cited

U.S. PATENT DOCUMENTS

| | | | | |
|---|---|---|---|---|
| 823,572 | A | * | 6/1906 | Wilson ........................ 241/278.1 |
| 1,329,199 | A | * | 1/1920 | Myers ......................... 222/181.2 |

(Continued)

FOREIGN PATENT DOCUMENTS

| | | |
|---|---|---|
| GB | 2064664 | 6/1981 |
| RU | 2385684 | 4/2010 |
| WO | WO 2008/021732 | 2/2008 |

OTHER PUBLICATIONS

PCT International Search Report for PCT/US2012/048561 mailed Feb. 15, 2013.

*Primary Examiner* — Patrick M Buechner
(74) *Attorney, Agent, or Firm* — Nicole J. Einerson

(57) ABSTRACT

A device for dispensing a dental substance. The device includes a cartridge for containing the dental substance. The cartridge has a plunger, and a dispensing opening. Further the device is operable to urge the dental substance toward the dispensing opening. The device further includes a cutter for cutting off a portion of the dental substance which protrudes over the dispensing opening. The device may particularly facilitate precise dispensation of a high viscosity dental substance.

20 Claims, 17 Drawing Sheets

(51) Int. Cl.
  *B65D 81/32* (2006.01)
  *B05C 17/005* (2006.01)
  *B05C 17/01* (2006.01)
  *B65D 83/00* (2006.01)

(56) References Cited

U.S. PATENT DOCUMENTS

| | | | | |
|---|---|---|---|---|
| 1,622,714 | A | * | 3/1927 | Grandt ............... 222/553 |
| 1,631,525 | A | * | 6/1927 | Gallett ............... 222/545 |
| 1,691,861 | A | | 11/1928 | Stout |
| 1,725,689 | A | * | 8/1929 | Witt ............... 222/553 |
| 1,738,220 | A | * | 12/1929 | Amsden ............... 222/553 |
| 1,956,558 | A | * | 5/1934 | Berry ............... 222/553 |
| 2,751,118 | A | * | 6/1956 | Soule ............... 222/80 |
| 3,339,810 | A | | 9/1967 | Block |
| 3,443,725 | A | | 5/1969 | Lawhorn |
| 4,366,919 | A | | 1/1983 | Anderson |
| 4,521,127 | A | * | 6/1985 | Tomburo et al. ............... 401/68 |
| 5,000,356 | A | * | 3/1991 | Johnson et al. ............... 222/391 |
| 5,301,842 | A | | 4/1994 | Ritter |
| 5,851,079 | A | * | 12/1998 | Horstman et al. ............... 401/174 |
| 6,039,483 | A | * | 3/2000 | Szekely ............... 401/50 |
| 7,086,564 | B1 | * | 8/2006 | Corrigan ............... 222/39 |
| 8,371,744 | B2 | * | 2/2013 | Walter et al. ............... 366/331 |
| 8,444,025 | B2 | * | 5/2013 | Greter et al. ............... 222/390 |
| 8,511,323 | B2 | * | 8/2013 | Jimenez et al. ............... 132/311 |
| 8,544,684 | B2 | * | 10/2013 | Perez ............... 222/39 |
| 8,590,747 | B2 | * | 11/2013 | Keller ............... 222/137 |
| 2007/0221683 | A1 | * | 9/2007 | Hohmann et al. ............... 222/207 |
| 2010/0282774 | A1 | * | 11/2010 | Greter et al. ............... 222/39 |
| 2011/0114668 | A1 | * | 5/2011 | Bublewitz et al. ............... 222/41 |
| 2012/0304991 | A1 | * | 12/2012 | Gotliboym et al. ....... 128/203.15 |

* cited by examiner

DEVICE FOR DISPENSING A DENTAL SUBSTANCE AND METHOD OF DISPENSING

CROSS REFERENCE TO RELATED APPLICATIONS

This application is a national stage filing under 35 U.S.C. 371 of PCT/US2012/048561, filed Jul. 27, 2012, which claims priority to EP Application No. 11175728.2, filed Jul. 28, 2012, the disclosure of which is incorporated by reference in its/their entirety herein.

FIELD

The invention relates to a device for dispensing a dental substance, and in particular to a device that is operable to extrude and cut off a portion of the dental substance. The invention further relates to a method of dispensing the dental substance.

BACKGROUND

A variety of dental substances are provided in packages which allow for storing the substances and enable the substances to be dispensed directly from the package. In particular dental impression materials are often provided in cartridges or bags which can be used in a motor powered device to dispense and mix portions of material from those. However for some applications it is desired to manually use and mix dental substances, and therefore some dental substances are provided in manually operable packages, like tubes or jars, for example.

Although such manually operable packages are available there is a need in dentistry to prepare dental substances at a relatively short time even in a situation in which a manual preparation is preferred. Further it is desirable to provide a package which is easy to use and which is relatively inexpensive.

SUMMARY

In one aspect, the invention relates to a device for dispensing preferably a dental substance. The device comprises a cartridge for containing the dental substance, and a plunger. The cartridge further has a dispensing opening. The device preferably comprises a screw mechanism which is operable to urge the dental substance toward the dispensing opening. Further the device comprises a closure which is adapted to openably close the dispensing opening. The closure comprises a cutter for cutting off a portion of the dental substance which protrudes over the dispensing opening. The closure has a closure wall through which an orifice extends, the closure and the cartridge being movable relative to each other between a closed position in which the closure wall covers the dispensing opening and an open position in which the dispensing opening and the orifice overlap at least partially.

In a further aspect the invention relates to a device for dispensing a dental substance. The device comprises a cartridge for containing the dental substance, and a plunger. The cartridge further has a dispensing opening. The device is operable to urge the dental substance toward the dispensing opening. The device particularly comprises a screw mechanism which is operable to urge the dental substance toward the dispensing opening. The screw mechanism is preferably operable by twisting the plunger and the cartridge relative to each other. The dental substance is a dental impression material (for example as described herein) or a component thereof.

The device of this aspect comprises an optional cutter for cutting off a portion of the dental substance which protrudes over the dispensing opening.

The invention is advantageous in that it preferably allows for providing a cut off portion of dental substance retained at the device. For example the invention may allow for a portion of the dental substance to be pre-portioned and thus to conveniently make that portion available to a user. The invention further may help metering the dispensation of a portion of the dental substance. Further the invention may allow a user to blindly dispense a desired portion of dental substance. The invention may further be advantageous in that it may help minimizing time for preparation of a dental substance before use. The invention further may provide for a device which is easy to use, and that is relatively inexpensive.

Although the present invention refers to a dental substance the device of the invention may instead of a dental substance be generally used for another pasty mass, like for example sealing compounds, bonding compounds, food, pharmaceuticals or cosmetics.

In one embodiment the device is adapted such that the dental substance can be urged toward the dispensing opening by moving the plunger and the cartridge relative to each other. The plunger may be received in a cartridge opening of the cartridge.

In a further embodiment the closure forms or comprises a handle by which the closure can be held and operated by a user of the device.

In one embodiment the screw mechanism is operable by twisting the plunger and the cartridge relative to each other. The plunger may be threaded and form part of the screw mechanism. For example the plunger and the cartridge may be thread connected. Therefore the cartridge and the plunger may together form the screw mechanism. For example the plunger may have an outer thread for engaging with a corresponding inner thread of the cartridge.

In an alternative embodiment the plunger may have an inner thread for engaging with a corresponding outer thread of the cartridge. For example the cartridge may comprise a screw which is rotationally fixed within and relative to the cartridge, and the piston may be screwed on the screw. Thus a rotation of the plunger and the cartridge relative to each other preferably causes the dental substance to be urged toward the dispensing opening. This is because the plunger and the cartridge due to the thread connection preferably displace relative to each other and that displacement preferably causes the dental substance to be urged toward the dispensing opening.

In a further alternative embodiment the plunger in combination with a piston forms a plunger assembly. The plunger and piston may together form the screw mechanism. In other words the plunger assembly may form the screw mechanism. The plunger assembly may be arranged within the cartridge such that the piston and the cartridge are rotationally retained relative to each other, and the piston and the plunger are rotatable relative to each other. Further the plunger and the cartridge may be axially retained relative to each other, and the piston and the cartridge may be axially displaceable relative to each other. The term "axially" in this regard preferably relates to a rotation axis of the plunger and cartridge relative to each other or a rotation axis of the piston and the plunger relative to each other. Thus a rotation of the plunger preferably causes the piston to displace axially, and accordingly to urge the dental substance toward the dispensing opening. The piston may comprise an inner thread and an inner cone and the spindle may comprise an outer thread and an outer cone. The device may be adapted such that the inner and outer cone in one position of the piston and the spindle relative to each other are in touch to seal a passageway through the piston forming the inner thread, whereas in another position of the piston and the spindle relative to each other the cones are spaced. Thus a relatively tight seal during storage of the device assembly may be achieved.

Any of the plungers described preferably have a handle by which the plunger can be held and operated by a user of the device.

In a one embodiment the device is adapted such that operating screw mechanism relative to the closure to urge the dental substance toward the dispensing opening also causes the closure to be urged toward the open position, and operating the screw mechanism reverse thereto causes the closure to be urged toward the closed position. In this regard operating the screw mechanism may comprise rotating the plunger and the cartridge (or the plunger and the closure) relative to each other. For example the device may be adapted such that the plunger relative to the closure and/or cartridge is rotatable in a dispensing direction in which the dental substance is urged toward the dispensing opening. The plunger rotated in the dispensing direction relative to the closure and/or cartridge preferably also causes the closure to be urged toward the open position. Further the plunger rotated in a direction opposite of the dispensing direction relative to the closure and/or cartridge preferably also causes the closure to be urged toward the closed position. For a rotation of the plunger relative to the closure and/or cartridge the plunger and the closure may be held by a user at both, the plunger handle and closure handle, and rotated against each other.

In one embodiment the closure is received on a front end of the cartridge which also preferably accommodates the dispensing opening. The closure preferably comprises or forms the cutter. The closure may have a closure wall through which an orifice extends. The orifice preferably forms an outlet of the device for the dental substance. This means that preferably the orifice forms the outermost opening of the device through which the dental substance flows upon dispensing. In particular the orifice may not open in a tube or passageway which has a further opening. Thus the device is preferably adapted for dispensing dental substance directly from the orifice. Preferably the closure and the cartridge form separate parts which are movable relative to each other between the closed position and the open position by sliding relative to each other.

In one embodiment in the closed position the closure wall may seal, for example hermetically seal, the dispensing opening. Further in the open position the dispensing opening and the orifice may overlap entirely, for example the dispensing opening may overlap the orifice entirely or vice versa.

In one embodiment the cartridge has a cartridge end face. The cartridge end face is preferably formed by an outer surface of the cartridge adjacent the front end of the cartridge. The cartridge end face may have a seal for sealing a gap between the cartridge end face and the closure. The seal may be arranged circumferentially around the dispensing opening. In particular the seal may be arranged adjacent the dispensing opening. Thus the dental substance is preferably sealingly encapsulated in the cartridge in the closed position of the device. Further the dental substance may be prevented from flowing between the cartridge and the closure during storage as well as during dispensation of dental substance.

In one embodiment the closure forms a cap which is adapted for receiving at least the front end of the cartridge. The cap and the cartridge may be retained relative to each other against separation but may be rotatable relative to each other. The closure further may form or comprise a handle by which the closure can be held and operated by a user of the device.

In one embodiment the closure has a through-hole through the closure wall which forms the orifice. The cutter may comprise a cutting edge formed by the closure wall. In particular the closure wall in the area adjacent the through-hole may form the cutting edge which at least partially delimits the orifice. The cutting edge may extend circumferentially, preferably entirely circumferentially, around the hole and thus the cutting edge may delimit the orifice. In particular the closure wall preferably tapers toward the orifice to form the cutting edge. The cutting edge may form a substantially sharp edge and the closure wall preferably smoothly tapers toward the cutting edge. For example the cutting edge may be formed by two surfaces which merge at an angle (measured between the surfaces inside the closure wall) of between about 5 degrees to about 30 degrees. Preferably the closure wall forms an outer surface of the device, for example an end face of the device. Further the orifice is preferably arranged adjacent the outer surface or end face of the device formed by the closure wall. The outer surface or end face of the device formed by the closure wall may form a receiving area for at least partially receiving the portion of the dental substance cut off. The receiving area may be generally flat or smooth, for example ball shaped, convex, or cylindrical, and directly accessible to a user of the device for removing a portion of the dental substance cut off. Further the cutting edge may be generally flush with the receiving area of the closure. Thus the closure wall may easily penetrate into a portion of dental substance dispensed over the orifice and the cut off portion may be removable from the receiving area.

In a further embodiment the cartridge end face is convex. The dispensing opening preferably extends through the cartridge end face. The cartridge end face may generally correspond in shape to a portion of an imaginary sphere. Therefore the cartridge end face may be generally spherical. However the cartridge end face may have other convex shapes or may be conical, for example may correspond to a cone or a truncated cone. Further the cutting edge may extend in an imaginary surface which corresponds in shape to the shape of the end face of the cartridge. For example the cutting edge may extend along a line on the imaginary sphere which the shape of the cartridge end face is based on. Thus the cutting edge and the cartridge end face preferably match in shape. This may provide for a seal between the cutting edge and the cartridge end face. Therefore the dental substance dispensed through the dispensing opening may be hindered in flowing between the cutting edge and the cartridge end face. The skilled person will recognize that the cartridge end face may have other shapes, although the convex shape has been found to be relatively convenient in use of the device by a user. In particular the cartridge end face may be generally planar.

In one embodiment the dispensing opening and the orifice have generally circular cross-sections. The dispensing opening and the orifice may have generally equal diameters, but preferably the orifice has a greater or slightly greater diameter than the dispensing opening. This preferably prevents a pressure to be exerted on the closure and thus may prevent the closure from lifting from the cartridge during dispensation of the dental substance. Further the device is preferably adapted such that in the open position the dispensing opening and the orifice are substantially concentrically aligned. However other shapes of the opening and the orifice are possible. Further the dispensing opening and the orifice may have different sizes and/or shapes.

Generally the closure may form a slide valve, in particular a rotary slide valve, with the cartridge. In this slide valve or rotary slide valve the closure may form a first valve member and the cartridge may form a second valve member. The first and second valve members may be rotatable about a valve rotation axis. The orifice and the dispensing opening may be arranged off-center of the rotation axis. For example the rotation axis may be arranged outside the orifice and the dispensing opening. The orifice may face in a direction away from the rotation axis. Preferably the orifice faces in a direction which is inclined relative to the rotation axis and inclined relative to a radial of the rotation axis. Further the rotation axis may be arranged generally parallel to a longitudinal axis of the device, and in one embodiment the rotation axis and the longitudinal axis may coincide. The skilled person will recognize that although a rotary slide valve is preferred another slide valve may form an appropriate equivalent, such as for example a linear slide valve.

In one embodiment the cartridge comprises a cartridge body and, separable therefrom, a cartridge insert. The cartridge insert preferably comprises a container for containing the dental substance, and a dispensing end comprising the dispensing opening. The cartridge insert further may be received at least with the container in the cartridge body. In particular the container may be received within the cartridge body with the dispensing end arranged outside the cartridge body. The cartridge insert may be received in one opening of the cartridge body and the plunger may be received in another opposite opening of the cartridge body. Thus the cartridge insert may be replaceable in the cartridge body by another cartridge insert, for example an empty cartridge insert may be replaceable by a new one. Accordingly the cartridge insert may form a disposable part of the device whereas other parts may be reusable. The closure may form part of the cartridge insert, for example may be fixed at the dispensing end of the cartridge insert. However the closure may further be separable from the cartridge insert, for example may be usable with different cartridge inserts.

In one embodiment the cartridge insert comprises a foil bag for holding the dental substance and a hood received on one end of the foil bag. The other end of the foil bag is preferably closed, for example by a closure clip. The hood preferably forms the dispensing end of the cartridge insert and the foil bag preferably forms the container for the dental substance.

In a preferred embodiment the device comprises at least a component of a type 0 dental impression material. Such a component as well as dental impression material prepared from two or more components are preferably generally non-sticky in accordance to ISO 4823. Preferably a portion of such a component or material may adhere but not stick at a surface. For example such a portion may be removable from a surface substantially without residues remaining on the surface. The skilled person will recognize that a non-sticky substance may still leave an optically recognizable print on a surface from which such portion was removed. This is in contrast to a substance which separates upon removal from a surface with a considerable sub-portion of the substance remaining of the surface.

In a further embodiment the device is adapted to provide an indication of a predetermined amount of dental substance being dispensed. The indication may comprise an audible click provided by ratchet. Further the ratchet may permit a relative rotation of the plunger or piston and the cartridge in the dispensing direction and restricting a rotation in the opposite direction. The ratchet may be provided by a detent at the plunger and a corresponding pawl at the cartridge, or vice versa. The detent may for example be formed by an outer groove in the plunger. The groove may extend in the plunger generally parallel to the longitudinal axis of the device. The ratchet may thus provide for an audible click at predetermined rotational positions of the plunger and the cartridge relative to each other. For example during a rotation of the plunger and the cartridge relative to each other the ratchet may provide one audible click per each full round (360 degrees rotation), per each half round (180 degrees rotation), or per any other suitable angle.

In one embodiment the rotation of the plunger and the cartridge relative to each other may be enabled in the opposite direction of the dispensing direction at a predetermined extent or at a predetermined extent only. For example the plunger and the cartridge may be freely rotatable in the dispensing direction but the rotation in the opposite direction may be limited to a predetermined rotation angle. Thus the plunger or piston may be retractable sufficiently to relief the dental substance from pressure built up during dispensation. However the retraction of the plunger or piston may be restricted such that air is prevented from being sucked in to the device. This may help avoiding the dental substance to alter due to interacting with the air during further storage in the device.

In one embodiment the cartridge is adapted for containing two dental substances. The cartridge is preferably adapted to contain the two dental substances separate from each other. The cartridge may have a further dispensing opening. Therefore the cartridge may have a first and a second dispensing opening. Accordingly the closure may have a further orifice for opening the further dispensing opening in the open position of the closure. Therefore the closure may have a first orifice and a second orifice for opening the first and second dispensing openings, respectively. In particular the cartridge may comprise a first chamber for holding a first dental substance and a second chamber for holding the second dental substance. The first chamber may open into the first opening and the second chamber may open in the second opening. Further a first plunger may be received or receivable within the first chamber for urging the first dental substance of the two dental substances toward the first dispensing opening. A second plunger may be received or receivable within the second chamber for urging the second dental substance of the two dental substances toward the second dispensing opening. Each of the first plunger and second plunger may correspond to the plunger of the invention, and thus may be threaded in one embodiment. However the plungers may alternatively cooperate with a common plunger for driving the first and second plungers. Such a common plunger may for example have an inner thread for engaging an outer thread of the cartridge. A rotation of the common plunger and the cartridge relative to each other in the dispensing direction preferably causes the first plunger and second plunger to be pushed by the common plunger toward the cartridge. Further the first plunger and second plunger may be pushed generally simultaneously toward the cartridge so as to generally simultaneously dispense the first and second dental substance. The first and second dental substances may form different components that are adapted for forming a hardenable dental material when merged.

In a further aspect the invention relates to a kit of parts which comprises at least two devices according to the invention. A first of the two devices contains a first dental substance and a second of the two devices contains a second dental substance. The first and second substances form different components that are adapted for, in combination, forming a hardenable dental material.

Such a hardenable material preferably is a dental impression material as describe herein.

In a further aspect the invention relates to a use of a device for dispensing a dental impression material or a component thereof. The device according to the use comprises a cartridge for containing the dental impression material or a component thereof, and a plunger. The cartridge further has a dispensing opening. The device of the use is operable to urge the dental impression material or a component thereof toward the dispensing opening. The cartridge and the plunger form a screw connection with each other and are rotatable relative to each other for dispensing dental impression material or a component thereof. The device of the use further optionally comprises a cutter for cutting off a portion of the dental impression material or a component thereof which protrudes over the dispensing opening.

Such a use may provide for relatively convenient dispensation and/or preparation of a dental impression material.

In a further aspect the invention relates to a method of dispensing a dental substance. The method comprises providing a device which comprises:
- a cartridge for containing the dental substance;
- a plunger;
- a dispensing opening;
- the device being operable to urge the dental substance toward the dispensing opening;
- wherein the device further comprises a closure for openably closing the dispensing opening; and
- the closure comprising a cutter for cutting off a portion of the dental substance which protrudes over the dispensing opening;
- twisting the closure and the plunger relative to each other in a dispensing direction and thereby causing the closure and the cartridge to rotate relative to each other from a closed position, in which the dispensing opening is closed, toward an open position, in which the dispensing opening is open;
- further twisting the closure and the plunger relative to each other in a dispensing direction and thereby causing a portion of the dental substance to be dispensed from the dispensing opening; and
- twisting the closure and the plunger relative to each other in a direction opposite of the dispensing direction and thereby cutting the portion of the dental substance.

In one embodiment of the method the device corresponds to the device of the invention in the form of any embodiment as disclosed herein.

The step of twisting the closure and the plunger relative to each other in a direction opposite of the dispensing direction may be performed automatically. For example the device may be adapted such that the closure is urged toward the closed position. The device may therefore have a spring or other elastic member which provides for closure to be urged toward the closed position. Preferably the spring or elastic force is selected such that the force is sufficient to cut the dental substance.

In one embodiment the method further comprises the step of twisting the closure and the plunger relative to each other in a direction opposite of the dispensing direction and thereby causing a pressure built up in the dental substance to reduce.

DETAILED DESCRIPTION

Figure 1:
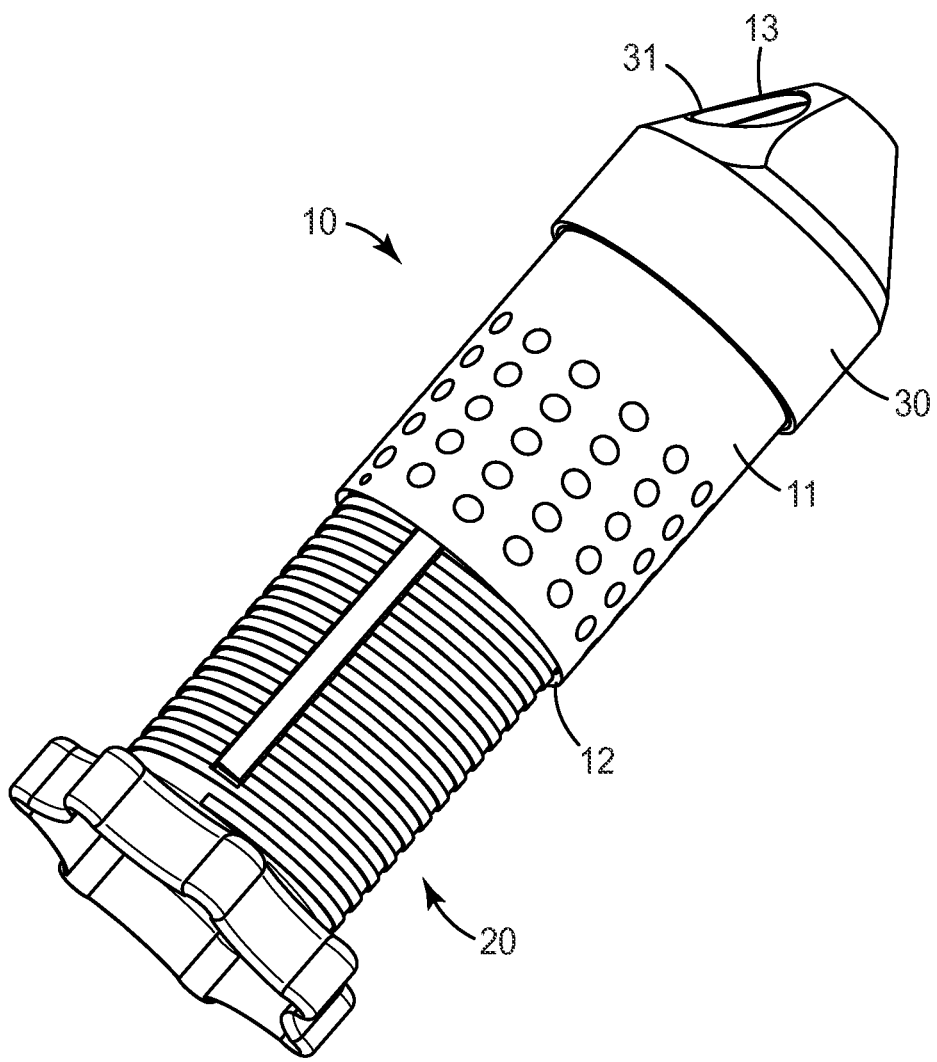
FIG. 1 is a perspective view of a device according to an embodiment of the invention.

FIG. 1 shows a device 10 for dispensing a dental substance. The device 10 comprises a cartridge 11 for containing the dental substance. The cartridge 11 has a cartridge opening 12 and a dispensing opening 13. The cartridge opening 12 and the dispensing openings 13 are arranged at opposite ends of the cartridge 11. In particular the dispensing opening 13 is arranged at a front end of the cartridge 11 and the cartridge opening 12 is arranged at a rear end of the cartridge 11. The cartridge opening 12 is closed by a plunger 20. In particular in the example shown the plunger 20 is received within the cartridge opening 12. The plunger 20 is movable relative to the cartridge 11, for example is movable into the cartridge 11 for extruding the dental substance from the cartridge 11 through the dispensing opening 13. The plunger 20 may be restricted to a movement into the cartridge 11 and blocked from a movement in the opposite direction. Thus a retraction of the plunger 20 and thereby suction of air into the cartridge can be avoided. The device 10 is particularly configured such that the plunger 20 is operable to urge the dental substance toward the dispensing opening 13. In the example shown the plunger 20 is thread connected with the cartridge 11. Therefore the plunger 20 can be rotated to urge the dental substance toward the dispensing opening 13. The device 10 further comprises a closure 30 which is adapted to openably close the dispensing opening 13. The closure 30 in the example implements a cutter 31 as explained in further detail below.

Figure 2:
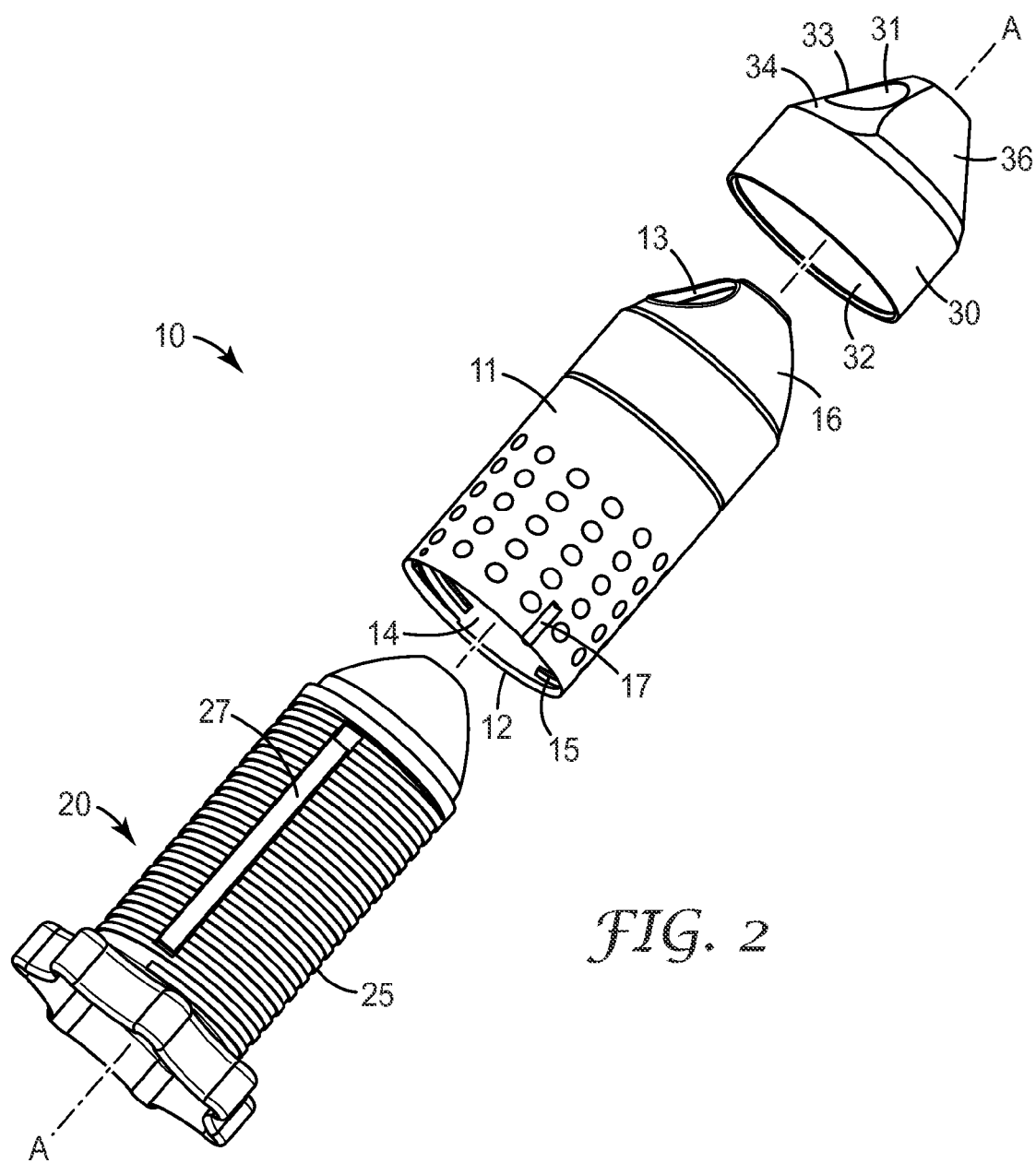
FIG. 2 is a perspective exploded view of the device shown in FIG. 1.

FIG. 2 is an exploded view of the embodiment shown in FIG. 1. The device 10 has a longitudinal axis A. The plunger 20 and the cartridge 11 extend along the longitudinal axis A and are adapted to be screwed into one another by rotation about the longitudinal axis A. The plunger therefore has an outer thread 25 and the cartridge 11 has an inner thread 15.

The outer thread 25 and the inner thread 15 are adapted to cooperate with each other, in particular are adapted to form a screw connection with each other. In the example the inner and outer threads 15, 25 correspond to a single-start thread, however a multiple start thread may be used in another example. A multiple start thread may allow relative rapid dispensation of a high viscosity dental substance.

The inner thread 15 is segmented over the thread circumference with the individual thread segments forming a non-threaded or generally non-threaded space between. In other words the inner thread is crossed by at least one groove 14 which extends generally parallel to the longitudinal axis A. The inner thread 15 in the example extends in three segments each extending over less than 120 degrees of the thread circumference, and such segments are separated by grooves extending along the longitudinal axis A.

The cartridge 11 further has a chamber which extends into the cartridge. In particular the chamber extends into the cartridge 11 from the rear end of the cartridge 11. The chamber therefore preferably opens in the cartridge opening 12 and the dispensing opening 12. The chamber in the example is at least partially formed by a cylindrical or generally cylindrical inner surface of the cartridge 11. The inner thread 15 protrudes from the inner surface of the cartridge 11. Preferably the inner thread 15 in a direction parallel to the longitudinal axis A extends from an area adjacent the cartridge opening 12 inwards into the cartridge 11, but may only extend over a part of the length of the inner surface. Thus the chamber preferably has a threaded section adjacent the cartridge opening 12 and a non-threaded section further remote from the cartridge opening 12. In the example the chamber has a threaded section adjacent the cartridge opening 12 and a non-threaded section adjacent the dispensing opening 13.

The skilled person will recognize that the chamber may be formed by alternatively shaped inner surfaces, for example by a surface which extends at a non-circular generally uniform cross-section into the cartridge 11. Such non-circular cross-section or profile may comprise a polygonal shape, an elliptical shape or any other suitable shape. It is noted that nevertheless thread structures may protrude from a non-cylindrical inner surface as long as such thread structures enable a screw connection with the outer thread 25 of the plunger 20.

For injection molding of the cartridge 11 a mould core may be used which has a larger cylindrical portion for forming the cylindrical section of the chamber and a smaller portion comprising negative thread structures to form the inner thread of the cartridge. The core may be retracted through the cartridge opening 12 which however requires the larger cylindrical core portion to be moved through a chamber area of the cartridge which is constricted by the thread 15. The cylindrical front portion may therefore have movable parts which allow the front portion to be at least partly contracted to make the larger core portion fit through the restricted area of the chamber. The grooves 14 in that regard enable that only some parts of the core have to be movable which helps minimizing the complexity of the design of such a core. Further this helps maximizing reliability of a mould comprising such core, and minimizing costs for making such mould. Thus the recesses 14 may allow the core to be configured such that it can be easily removed.

The cartridge 11 of the device 10 has a cartridge end face 16 through which the dispensing opening 13 extends. The cartridge end face 16 in the example has a convex shape, and in particular is preferably generally spherical. The closure 30 has an inner surface 32 which is shaped such that the cartridge end face 16 can be received within the closure 30. In other words the closure 30 and the cartridge 11 are configured such that they can be mated. Preferably the inner surface 32 of the closure 30 and the cartridge end face 16 are adapted for substantially matching in shape. Further the closure 30 has an orifice 33. In a situation in which the closure 30 and the cartridge 11 are mated the closure 30 and the cartridge 11 are preferably rotatable relative to each other between an open position and a closed position. In the open position the orifice 33 may at least partially overlap the dispensing opening 13. Preferably the orifice 33 entirely clears the dispensing opening 13 in the open position. Thus an outlet for the dental substance may be formed. In the closed position the dispensing opening 13 may be covered, preferably entirely covered, by a wall 34 of the closure 30. Further in the closed position the orifice 33 may also be covered, preferably entirely covered, by the cartridge end face 16. Thus the dental substance may be sealed within the cartridge. Further the cartridge end face 16 may have a seal (not shown), for example an elastic lip seal, adjacent the dispensing opening 13. The lip seal may further be rigid or elastic and the closure may have at least an elastic portion for sealing with the lip seal. The seal may seal a gap between the closure 30 and the cartridge end face 16. In summary the closure 30 and the cartridge 11 in combination form a rotary slide valve. In this rotary slide valve the closure 30 and the cartridge 11 are rotatable relative to each other about the longitudinal axis A and the rotary slide valve comprises the dispensing opening 13 and orifice 33 in a off center relation ship to the longitudinal axis A. Therefore a rotation of the closure 30 and the cartridge 11 relative to each other provides for the dispensing opening 13 and the orifice 33 to move relative to each other, for example in an open position in which the dispensing opening and the orifice overlap, and a closed position, in which the dispensing opening and the orifice are offset. The rotary slide valve thus preferably allows for openably closing the dispensing opening 13 of the device 10.

The device 10 may be adapted such that the closure 30 is urged toward the closed position. For example the closure 30 may be urged toward the closed position by spring force. Therefore the device 10 may have a spring or other elastic member providing for the closure 30 to be urged toward the closed position.

The closure 30 further has an outer surface 36 which is at least partially conical or convex. Further preferably the orifice 33 extends through outer surface 36. Therefore the portion of the dental substance dispensed from the orifice 33 may protrude from the device in a direction which is inclined relative to the longitudinal axis A and inclined relative to a perpendicular of longitudinal axis A. It has been found that this provides the portion dispensed to retain relatively reliably even if the device is deposited in different orientations, for example placed on a dentist's desk with the longitudinal axis A of the device oriented horizontally or vertically.

The cartridge 11 in the example further has a pawl 17 for permitting a rotation of the plunger 20—in a situation where the plunger 20 is mounted in the cartridge 11—in only one direction. The plunger 20 has a groove 27 for engaging with the pawl 17. The pawl 17 and the groove 27 are adapted for allowing a rotation of the cartridge 11 and the plunger 20 in a dispensing direction, and for interlocking with each other with regard to a rotation of the cartridge 11 and the plunger 20 in an opposite backward direction. Thus the pawl 17 and the groove 27 may in combination form a ratchet. The dispensing direction preferably corresponds to a direction in which the cartridge 11 and the plunger 20 are rotated for dispensing the dental substance from the device 10. A rotation in the dispensing direction preferably causes the pawl 17 and the groove 27 to provide an audible click as the pawl 17 and the groove 27 engage and disengage during rotation. The rotation of the plunger 20 and the cartridge 11 relative to each other over a certain angle in the dispensing direction causes a proportional amount of dental substance to be dispensed (due to the thread connection with the cartridge). For example a full turn of the plunger 20 (rotation by 360 degrees) may cause dispensation of a sufficient amount of dental substance for one application. Therefore the plunger 20 having one groove 27 may in combination with the pawl 17 provide for an audible click per 360 degrees of rotation of the plunger 20 and the cartridge 11 relative to each other, or one audible click per one predetermined portion of dental substance dispensed. The device 10 thus may generally allow an operator to meter a desired amount of a dental substance by counting the number of clicks. This may enable generally blind operation of the device, and thus may facilitate operation.

The skilled person will be aware that additionally in the same embodiment or in an alternative embodiment a pawl may be arranged at the plunger and a corresponding detent, for example groove, may be arranged at the cartridge. More than one detent and/or pawl may be present. For example two, three, four or more detents may be present generally uniformly distributed over the circumference of the plunger 20 and/or the cartridge 11. Generally the device 10 may have any kind of ratchet which allows the plunger 20 and the cartridge 11 to be rotationally positioned relative to each other at one or more predetermined angular positions. Such a ratchet may provide an audible indication which may allow a user to recognize such a position and/or the related amount dispensed. Further such a ratchet may restrict the rotation of the plunger 20 and the cartridge 11 in one direction.

Further the skilled person will recognize a variety of alternatives or modifications of the above described examples which all may provide a device which is adapted to provide an indication of a predetermined amount of dental substance being dispensed.

Figure 3:
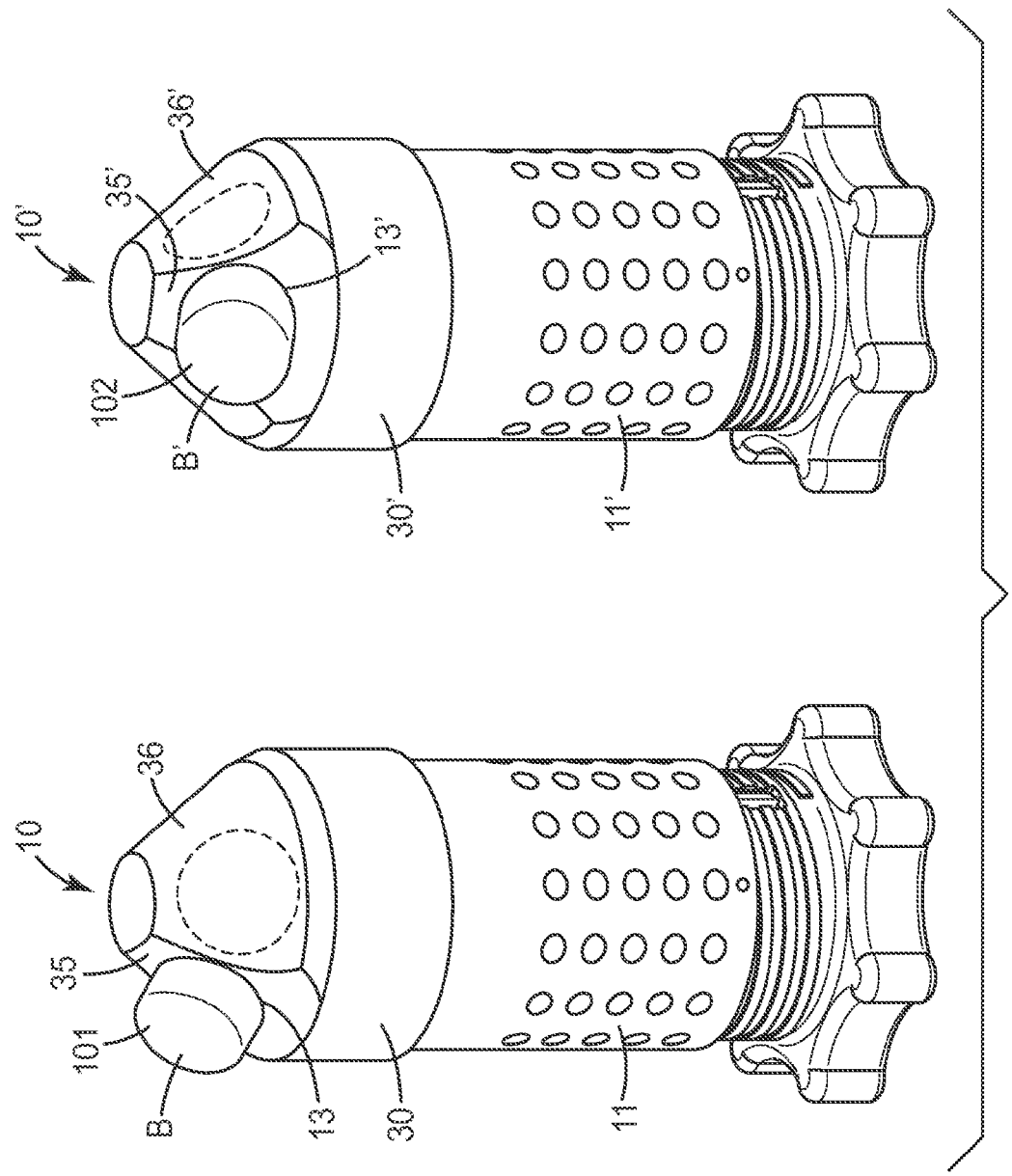
FIG. 3 is a perspective view illustrating devices according to an embodiment of the invention.

FIG. 3 shows the device 10 and a further device 10' each containing a component of a dental impression material. The components may be mixed subsequent to a dispensation from the devices 10, 10', for example merged and kneaded by hand, and together may form a hardenable dental impression material. A first portion 101 of a first component B protrudes from the dispensing opening 13 of the device 10 and a second portion 102 of a second component B' protrudes from the dispensing opening 13' of the device 10'. The first portion and/or second portion 101/102 may be cut off to separate these from the device 10/10' by rotating the cartridge 11/11' and the closure 30/30' relative to each other. Thereby the closure 30/30' laterally penetrates into the protruding strand of the respective component, separates it from the device, and finally the cut portion of the component is preferably at least partially received on an outer surface 36/36' of the closure 30/30' in a receiving area 35/35'. Each of the components preferably is a high viscous flowable paste, and exhibits a self-supporting and non-sticky consistency. This means that the components are preferably adapted such that at about room temperature (approximately 23° C.) they can be extruded from the dispensing opening 13/13' of the device 10/10' and such that an extruded strand of a certain cross-section and length remains generally in position without substantially deforming. For example a strand having a diameter of about 15 mm and a length of about 20 mm may remain generally in position without substantially deforming over a time of about 10 minutes. Further the device including the respective component may be adapted such that a cut component portion adheres at the device 10 without however sticking to the device 10. Thus the cut portions 101/102 preferably remain generally in position after cutting, for example preferably do not fall off after cutting. Therefore a user, for example a dentist or a dentist's assistant, may prepare portions of the components and keep the so prepared portions available directly on the device. This may be advantageous in that the components may be prepared at desired quantities separate from each other and merged only shortly before use. This may minimize time for preparing the impression material during a dental treatment, for example.

The devices 10/10' may have different sizes. In particular one of the devices 10/10' may be placeable into the other one of the devices 10/10'. This may for example be achieved by one device 10/10' providing a hole in the plunger in which the other device 10/10' may be received. Thus the space for storing a set of two or more devices may be minimized.

In one embodiment the dental substance is one of at least two components A and B of a dental impression material. The component or both components may consist of condensation cured or addition cured silicones which exhibit a consistency which can be kneaded by hand. Thus the components can be merged or mixed by a user, for example a dentist or dental assistant, by hand kneading. The components are further preferably adapted such that they can be relatively homogeneously mixed. The so prepared mixed dental impression material may be filled in a dental impression tray and placed in a patient's mouth for making a dental impression. The prepared dental impression material may be substantially non-sticky, for example may not stick to the device of the invention, meaning that the prepared dental impression material may be removable from a surface of the device generally without leaving residues behind.

The dental substance may therefore generally exhibit a consistency as it is described by ISO 4823 as kneadable or putty or type 0 consistency. ISO 4823 describes four different impression molding consistencies, namely a readily flowing consistency (type 3), a medium-flowing consistency (type 2), a poorly flowing consistency (type 1) and a kneadable consistency (type 0). For this purpose it is important that these type 0 materials do not stick to the fingers or gloves and/or leave residues behind. It is typical for these materials to have a high viscosity or consistency in the mixed paste which can be measured according to ISO 4823 and which shows a value of max. 35 mm. Such a high consistency can be achieved by using a high filler load or high viscous silicone polymers in the formulations of A and B.

The dental substance may further comprise an isoparaffin or paraffin wax or microwax and/or liquid paraffin or liquid paraffin-coated fillers. This prevents the pastes sticking to the fingers. Materials of this nature are described, for example, in EP-A 0 219 660, EP-A 0 166 107, EP-A 0 158 141, EP-A 0 152 887 and U.S. Pat. No. 7,186,758 B2.

Condensation cured silicones generally consist of a silicone oil based on a polydimethylsiloxane containing hydroxyl end groups and mixed with fillers and a curing component containing a metal salt, e.g. of a monocarboxylic acid and a silicic acid ester as a crosslinking component. Examples of metal compounds are Dibutyltindilaurate or Titaniumalkoxides.

Preferred are addition curing silicones containing at least one organopolysiloxane having at least two unsaturated groups in the molecule, at least one organohydrogenpolysiloxane having at least or more than two SiH-groups in the molecule, a platinum catalyst, fillers and additives like those described to reduce stickiness but also pigments, plasticizers, antioxidants or surfactants.

The type 0 (ISO 4823) materials can also be based on condensation or addition curing polyethers and polyethersilicones. They are available in two components A and B which are mixed in a volume ratio of typically 10:1 to 1:10, preferably 1:1.

Figure 4:
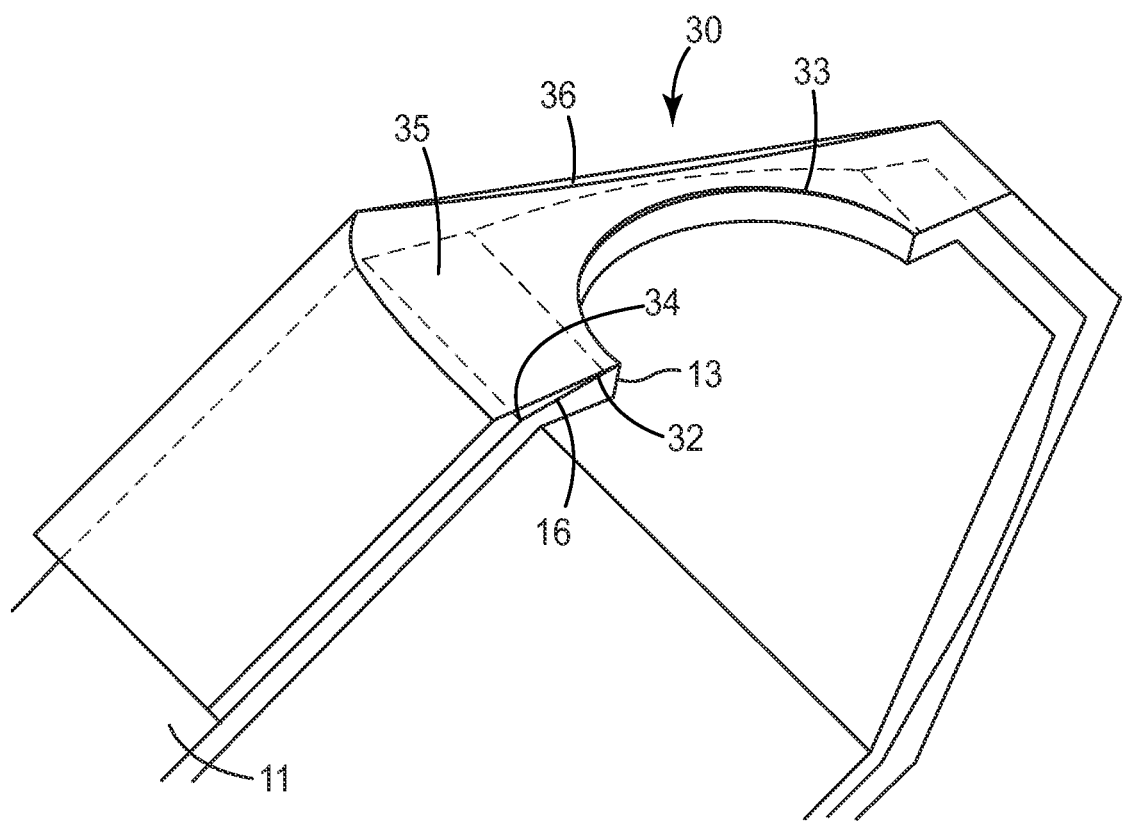
FIG. 4 is a partial perspective view of a device according to a further embodiment of the invention.

FIG. 4 shows the closure 30 in relation to the cartridge 11 in more detail. The closure 30 and the cartridge 11 are shown in the open position with the dispensing opening 13 and the orifice 33 aligned with one another and forming an outlet for the dispensing device 10. The orifice 33 extends through the wall 34 of the closure 30. The wall 34 tapers toward the orifice 33 to form a relatively sharp edge forming a cutting edge. In other words the orifice 33 in the example is formed by a cutting edge. The cutting edge preferably allows for a dental substance eventually extruded through the dispensing opening 13 from the cartridge to be cut upon relative rotation of the closure 30 and the cartridge 11 toward the closed position. The cutting edge is preferably shaped such that it matches in shape with the convex portion 16 of the cartridge 11. Thus the cutting edge may generally correspond in shape to a line on an imaginary sphere, and the convex portion of the cartridge end face 16 may generally correspond in shape to the same imaginary sphere. Therefore the cutting edge and the convex portion 16 may be shaped to exactly or essentially exactly match with each other. This preferably provides a good seal between the cutting edge and the cartridge end face 16. For example such a good seal may be particularly formed in the open position of the cartridge 11 and the closure 30. Accordingly the dental substance extruded from the cartridge may be hindered in flowing between the closure 30 and the cartridge end face 16 of the cartridge 11. Further thus a relatively precise cutting of the dental substance extruded from the cartridge 11 over the dispensing opening 13 may be enabled.

In the example the orifice 33 is formed by a generally spherical recess extending from the inner surface 32 of the closure 30 through the closure wall 34 toward the receiving area 35. Further in the example the receiving area 35 is of generally spherical shape. The spherical shape of the receiving area 35 is preferably based on a sphere having a larger diameter than a sphere which the shape of the recess is based on. Thus the orifice 33 is formed in the receiving area 35. In other words the cutting edge is generally flush with the receiving area 35 of the closure 30. This helps the closure 30 to easily penetrate into the dental substance.

Because both, the receiving area 35 and the recess are of spherical shape, the intersection of those spherical shapes provide the orifice 33 with generally circular shape. The skilled person will recognize that the receiving area 35 may alternatively be generally planar to form a circular orifice. Further in case a non-circular orifice is acceptable the receiving are 35 may have any other desired shape which is suitable to serve as an area to receive and retain the dental substance cut off.

In an example (not shown) the orifice opens into an open well from which the dental substance dispensed and cut may be removable, for example by a user. The well may have a closure lid which may close the well during dispensation for metering a predetermined amount of dental substance within the well. The predetermined amount may correspond to the capacity of the closed well.

Figure 5A:
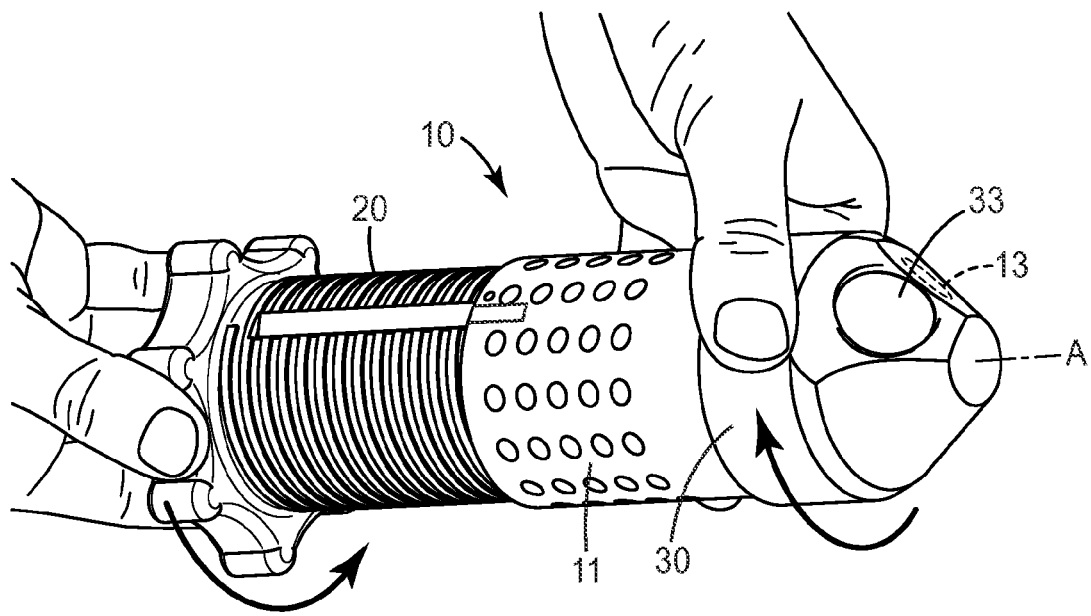
FIGS. 5a-5d are perspective views illustrating an operation of a device according to an embodiment of the invention.
Figure 5B:
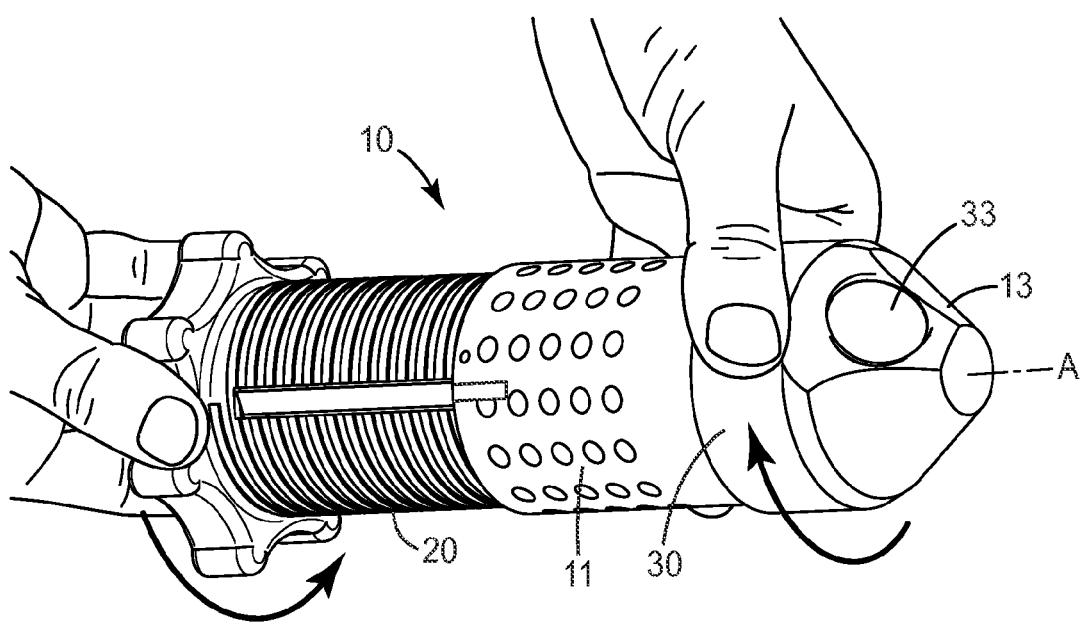
Figure 5C:
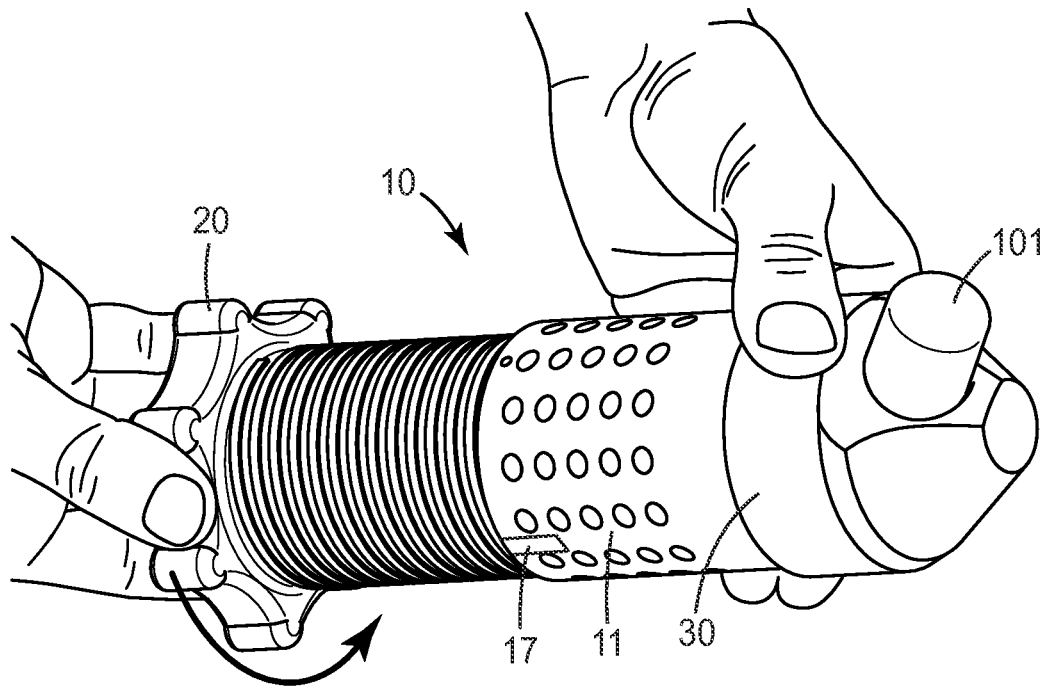
Figure 5D:
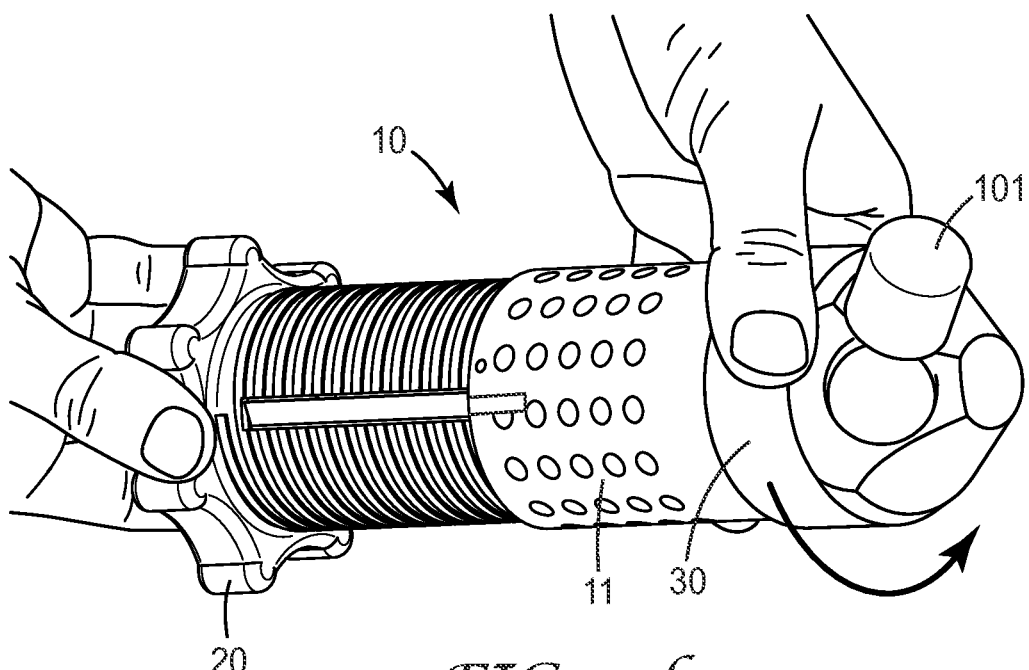

FIGS. 5a to 5d illustrate an operation of the device 10. In FIG. 5a the device is shown in the closed position in which the orifice 33 is placed in a non-overlapping relationship with the dispensing opening 13 (not visible, indicated with dashed lines). Therefore the closure 30 entirely seals the dispensing opening 13. In the position shown the device 10 may be suitable for storing the contained dental substance encapsulated from the environment in the device 10. As indicated by the arrows the closure 30 and the plunger 20 are twisted relative to each other toward the dispensing direction. The dispensing direction in the example corresponds to a direction of a clockwise rotation of the plunger 20 relative to the cartridge 11 or the closure 30 around the longitudinal axis A. In particular a torque around the longitudinal axis A is applied between the closure 30 and the plunger 20 in the dispensing direction. In the example the torque is applied by one hand holding the closure 30 and the other hand holding the plunger 20 and urging the closure 30 and the plunger 20 for rotation against each other. The device is adapted such that the cartridge 11 and the closure 30 rotate relative to each other at a lower force than the plunger 20 and the cartridge 11. The device further preferably has rotation stops which enable a rotation of the closure 30 and the cartridge 11 relative to each other in an area between the open and closed position and stop a further rotation toward an outside of that area. Thus twisting the closure 30 and the plunger 20 toward the dispensing direction preferably firstly causes the closure 30 and the cartridge 11 to rotate relative to each other while the cartridge 11 and the plunger 20 preferably do not rotate until the device is in the open position as shown in FIG. 5b. In the open position the closure 30 and the cartridge 11 preferably are stopped from further rotating relative to each other by one of the stops so that further twisting preferably causes the plunger 20 and the cartridge 11 to rotate relative to each other. A rotation between the cartridge 11 and the plunger 20 preferably also causes a portion 101 of the dental substance to be dispensed from the outlet of the device 10 as shown in FIG. 5c. In the position shown in FIG. 5c the plunger 20 is placed further within the cartridge 11 relative to the position shown in FIG. 5b. Further in the position shown in FIG. 5c the device is still in the open position. The amount of dental substance dispensed may be metered by counting the amount of audible clicks provided by the pawl 17 and the groove 27.

For cutting the portion 101 the device 10 may be twisted backwards. In particular the closure 30 and the plunger 20 may be twisted opposite to the dispensing direction. Again this preferably firstly causes only the closure 30 and the cartridge 11 to rotate until the device 10 is in the closed position. Thereby the portion 101 of the dental substance is cut, but preferably retains at the device. Once the device is in the closed position the closure 30 and the cartridge 11 are stopped and further twisting preferably urges the plunger 20 and the cartridge to be rotated backwards. However due to the pawl 17 and the groove 27 a backward rotation between the plunger 20 and the cartridge is restricted so that a backward rotation of the plunger 20 and the cartridge 11 is limited. Thus suction of air into the device, which may adversely affect the dental substance, may be avoided.

On the other hand the pawl 17 and the groove 27 may be adapted to enable a predetermined backward rotation between the plunger 20 and the cartridge 11 in a situation in which the pawl 17 and the groove 27 are engaged. Therefore the plunger 20 may be retracted from the cartridge 11 over a predetermined distance. The predetermined distance may be selected such that pressure in the dental substance built up during dispensing may be removed but air still is not sucked into the device. Therefore the device may be depressurized along with the backward twisting for cutting off the dental substance. This may be advantageous in that uncontrolled flow of the dental substance due to overpressure trapped in the device upon opening of the device may be avoided.

In one example the device 10 (or other devices disclosed herein) may be provided with a mount, for example a wall mount. Thus the device may be fixed at a desired place, for example in a dentist's practice, and operated with only one hand. The device may for example be held in place at the cartridge and the plunger may be operable relative to the device. Accordingly two devices for dispensing two components of a dental material may be operated each by one hand simultaneously by one user. This may help minimizing time for preparation of the dental material, for example and further may help saving space in a dental practice.

Figure 6A:
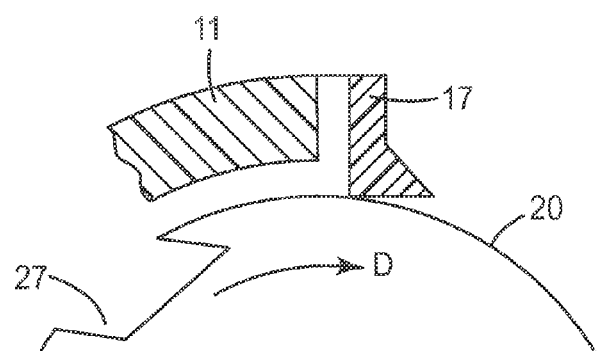
FIGS. 6a-6d are cross-sectional partial views of a device according to a further embodiment of the invention.
Figure 6B:
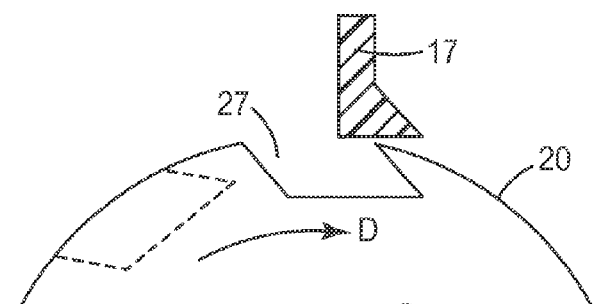
Figure 6C:
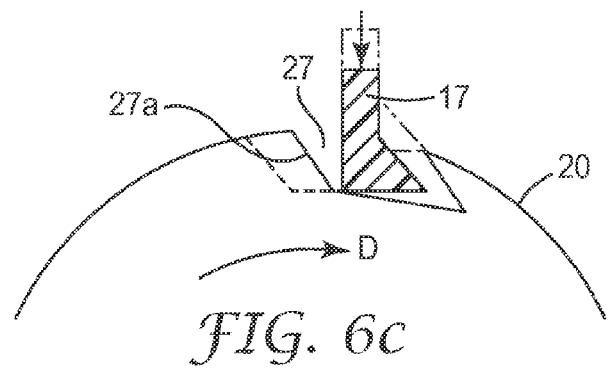

FIGS. 6a to 6d show an operation of an exemplary pawl 17 and a groove 27 in a cross-sectional partial view of the plunger 20 and the cartridge 11. The pawl 17 and a groove 27 in the example enable such backward movement over a predetermined distance after engaging. FIG. 6a shows the pawl 17 and the groove 27 disengaged, whereas FIG. 6c illustrates a situation in which the pawl 17 and the groove 27 are engaged. The groove 27 and the pawl 17 are adapted for automatically engaging and disengaging during a rotation of the plunger 20 relative to the cartridge 11 in the dispensing direction (indicated by "D"). The pawl 17 is preferably spring loaded toward the engaged position. Thus the pawl 17 may audibly snap into the groove 27 as the pawl 17 and the groove 27 are suitably positioned for engaging.

In the example the groove 17 has an inclined flank 27a which guides the pawl 17 out of the groove upon rotation of the plunger 20 relative to the cartridge 11 in the dispensing direction. The skilled person will recognize that instead or in addition the pawl may have an inclined surface providing the same effect. Further the skilled person will know other solutions for providing the same or similar effect.

Figure 6D:
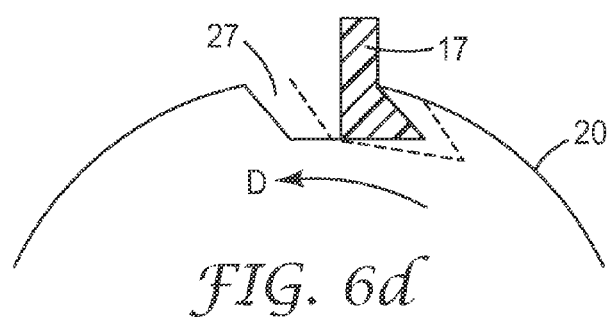

Further the groove 27 and the pawl 17 are adapted such that in a position of the plunger 20 and the cartridge 11 relative to each other in which the pawl 17 and the groove 27 are enabled for engaging (as illustrated in FIG. 6c) additionally a backward movement of the plunger 20 relative to the cartridge 11 is enabled in a position of the pawl 17 and the groove 27 being engaged. In the example this is provided by a generally L-shaped structure of the pawl 17 which cooperates with a complementary L-shaped structure of the groove 27. This L-shaped structure further provides for interlocking the pawl 17 and groove 27 once engaged with each other upon a rotation of the plunger 20 and the cartridge 11 relative to each other as illustrated in FIG. 6d. FIG. 6b shows the same position of the plunger 20 and the cartridge 11 but with the pawl 17 and the groove 27 disengaged. Starting from FIG. 6b the situation of FIG. 6d is reached by a rotation of the plunger 20 and the cartridge 11 in the dispensing direction D until the pawl 17 and the groove 27 are engaged, and by a subsequent rotation backwards until the pawl 17 and the groove 27 are interlocked. Thus a ratchet engaging at predetermined positions of the plunger 20 and the cartridge 11 is implemented which further provides a predetermined backward rotation from these predetermined engaging positions.

Figure 7:
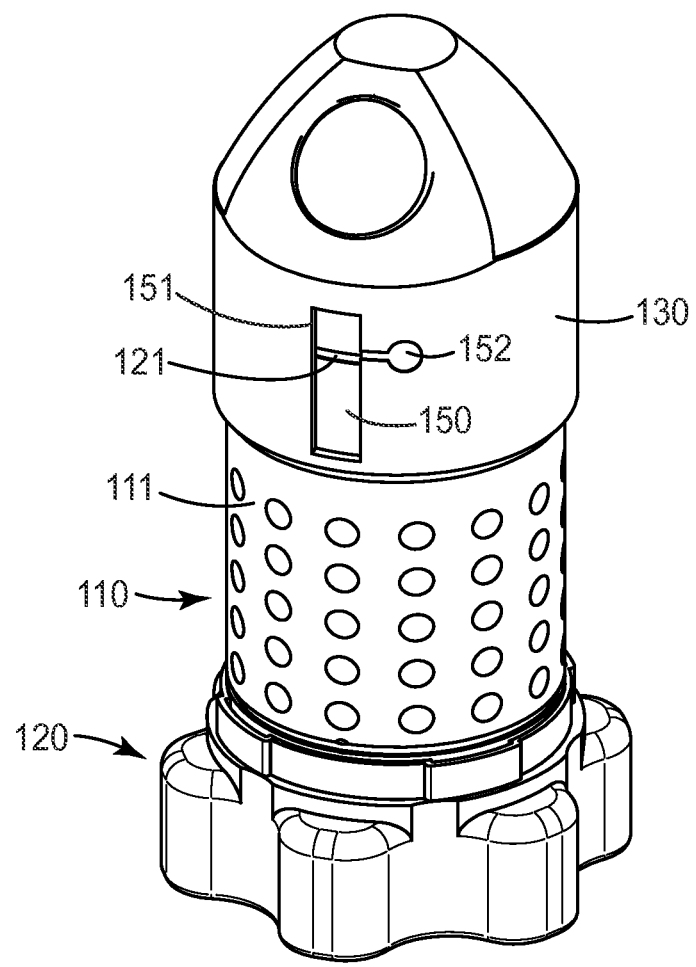
FIG. 7 is a perspective view of a device according to a further embodiment of the invention.

FIG. 7 shows a device 110 according to a further embodiment of the invention. The device 110 has a cartridge 111 and a closure 130 which are adapted for cooperation as disclosed in the examples illustrated in FIGS. 1 to 6d. However the device 110 relative to the device illustrated in FIGS. 1 to 6d has a plunger assembly 120 in the alternative of the plunger described above.

The device 110 further comprises an "advance empty" indicator 150. Such indicator preferably gives a user an indication in advance to the device becoming empty. For example such indication may be provided in case the amount of dental substance in the device approaches an amount typically needed for a dental treatment so that the user can hold a fresh device available before using the almost empty device. The indicator may be formed by a transparent or translucent area in the cartridge 111 through which the piston 121 is visible as it approaches the cartridge front end. In the example the closure 130 has a window 151 through which the transparent or translucent area in the cartridge 111 may be observed. However the closure 130 may further be transparent or translucent or may have a transparent or translucent area. The device 110 further has an advance empty marking 152 which indicates the position of the piston 121 from which on the remaining available amount of dental substance is less than the amount typically needed for one dental treatment. The advance empty indicator may therefore roughly indicate the fill level the device and further give particular indication about a predetermined amount of remaining dental substance. The advance empty indicator may therefore facilitate the use and application of the dental substance.

Figure 8:
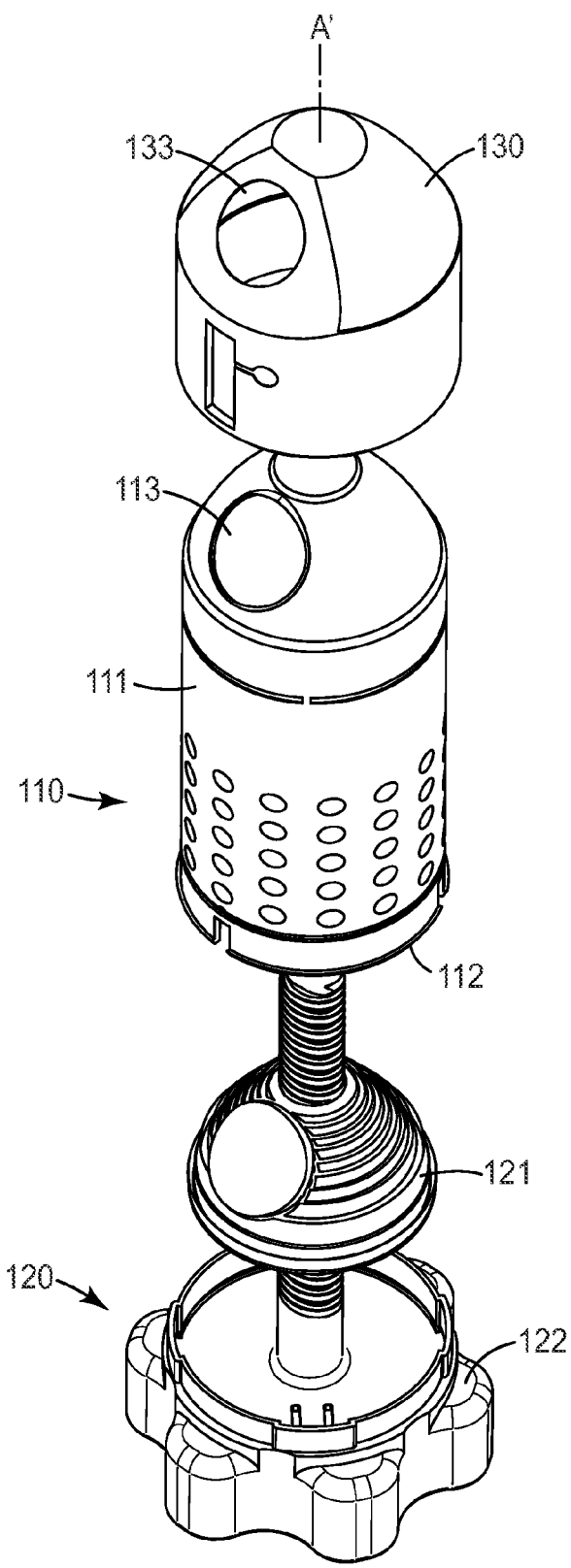
FIG. 8 is a perspective exploded view of the device shown in FIG. 7.

FIG. 8 shows the device 110 in an exploded view. The cartridge 111 has a cartridge opening 112 and a dispensing opening 113. The plunger assembly 120 and the cartridge are adapted such that the plunger assembly 120 can be received within the cartridge opening 112 of the cartridge 111. Further the closure 130 and the cartridge 111 are adapted for cooperation with one another in that the closure 130 and the cartridge 111 can be positioned in a closed position and an open position with one another. In the closed position the closure 130 covers, preferably entirely covers, the dispensing opening 113 of the cartridge, and in the first position an orifice 133 of the closure overlaps at least partially, preferably entirely overlaps, with the dispensing opening 113. Thus the overlapping dispensing opening 113 and orifice 133 form an outlet of the device in the open position. The outlet preferably allows a dental substance stored in the device 110 to be dispensed. The cartridge 111 and the closure 130 are preferably adapted such that they can be mated and in the mated position are movable, in particular rotatable, relative to each other between the open and the closed position. The movement or rotation of the closure 130 and the cartridge 111 relative to each other is preferably limited to an area between the open and the closed position and blocked outside. Stops (not shown) in the device 110 preferably provide for such limitation. Further the closure 130 also comprises a cutting edge forming the orifice 133 and allowing for a portion of the dental substance protruding from the dispensing opening 113 to be cut.

The plunger assembly 120 has a piston 121 and a plunger 122 which together form a screw connection. Thus a rotation of the plunger 122 and the piston 121 relative to each other preferably causes the plunger 122 and the piston 121 to displace relative to each other in a dimension parallel to the longitudinal axis A'. The piston 121 and the cartridge 111 are preferably retained against twisting relative to each other in the assembled device (as illustrated in FIG. 7). In one example the piston 121 and the cartridge 111 are retained against twisting generally by friction. For example the piston 121 and the cartridge 111 may be press fitted with one another. However the device 110 may further comprise an anti twist lock for locking the piston 121 and the cartridge 111 against rotation relative to each other. Further the piston 121 and the cartridge 111 are preferably movable longitudinally (along the longitudinal axis A') relative to each other in a situation in which the piston 121 is received within the cartridge 111. In this situation the piston 121 may be moved in a direction from the cartridge opening 112 toward the dispensing opening 113 to dispense the dental substance from the dispensing opening 113 in the open position of the device. The movement of the piston 121 can preferably be caused by rotating the plunger 122. The plunger 122 is preferably retained at the cartridge 111 against longitudinal displacement (in a dimension parallel to the longitudinal axis A') so that a rotation of the plunger 122 causes longitudinal movement of the piston 121. Therefore the plunger assembly 120 comprises the piston 121 which is longitudinally movable within the cartridge 111 but retained against rotation relative to the cartridge 111, and a plunger 122 which longitudinally retained but rotatable relative to the cartridge 111.

The device 110 preferably provides for a constant length of the device 110 independent from the fill level of the dental substance stored therein. This is because the plunger 122 and the cartridge 111 may be axially retained and only the piston 121, driven by the plunger 122, may axially move inside the cartridge 111 without extending outside of the cartridge 111.

Figure 9:
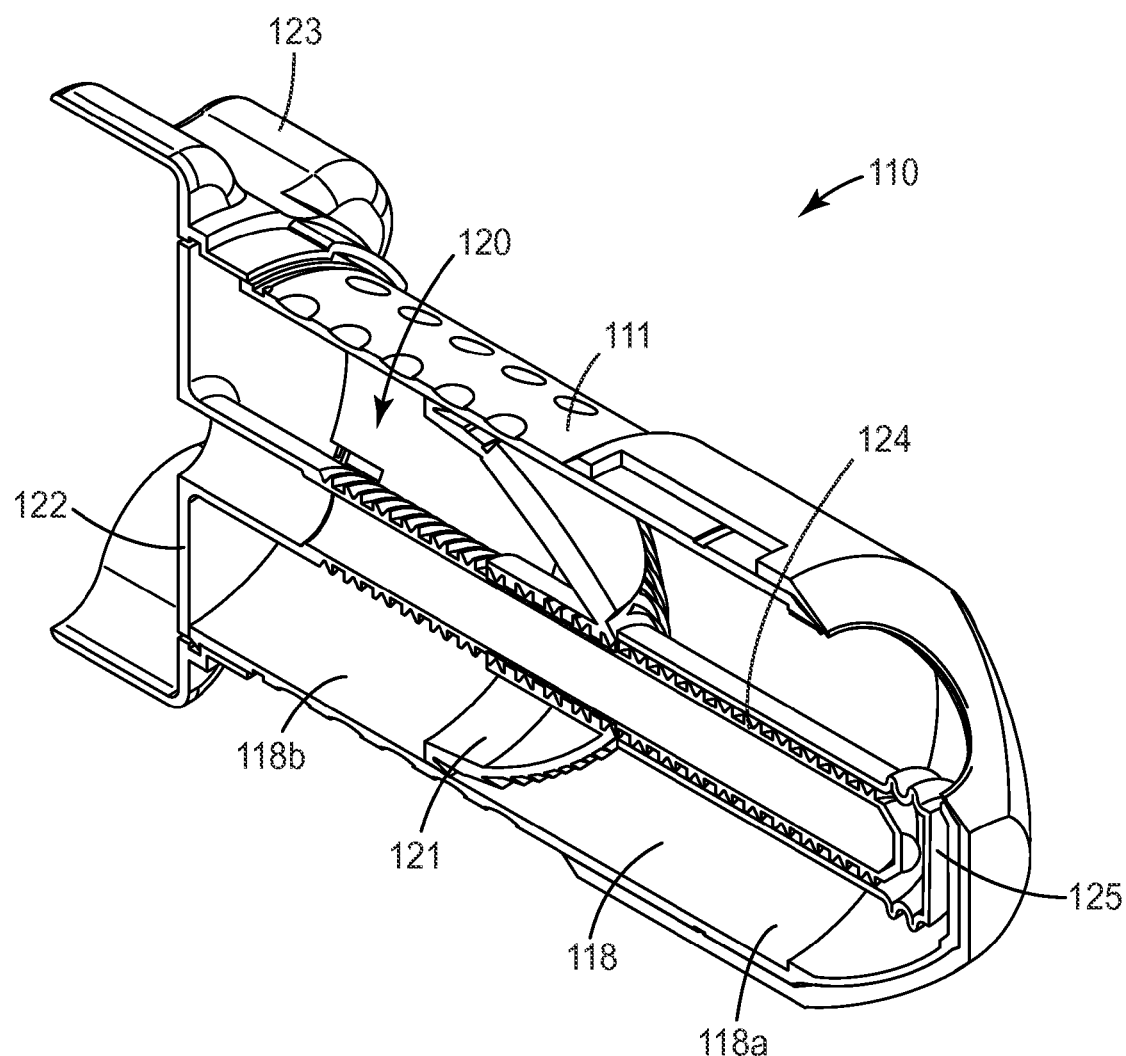
FIG. 9 is a perspective cross-sectional view of the device shown in FIG. 8.

FIG. 9 shows in a cross-sectional view of the device 110 more detail about the plunger assembly 120 in relation to the cartridge 111. The plunger 122 has a handle 123 and a spindle 124. The spindle 124 is threaded and engages with a thread provided in the piston 121. The device has a chamber 118 for containing a dental substance to be dispensed, for example a dental substance of a dental impression material. The chamber 118 is divided by the piston 121 into a front partition 118a which may be (generally entirely) filled with the dental substance and a generally empty rear partition 118b. The spindle 124 depending on the fill level of the dental substance in the device 111 may extend into the front partition 118 and thus into the dental substance. Therefore a relative compact design for the device 111 is enabled. The piston 121 optionally has a protection sleeve 125 into which the spindle 124 extends and which prevents direct contact between the spindle 124 and the dental substance. The protection sleeve 125 may be flexible such that it can be compressed as the piston 121 is moved for dispensing the dental substance. The protection sleeve 125 may be sealingly fixed at the piston 121 and is preferably closed at the opposite side. This may allow for the plunger 122 to be kept uncontaminated from the dental substance and therefore may allow for the plunger 122 to be reused, whereas the remainder of the device 110 may be disposable.

The diameter of the spindle may be selected to control the capacity of the chamber 118, in particular the chamber 118a. Therefore also the amount of dental substance dispensed per rotation of the spindle may be controlled. This preferably allows for designing multiple devices generally identical, but just with different plunger assemblies. This may be advantageous for providing devices largely having parts of the same or similar design, but which provide for different ratios between the rotation of the plunger assembly and the amount of dental substance dispensed. For example a set of two devices for dispensing two dental substances to be mixed together at different mixing ratios (e.g., 2:1) may be provided by two largely similar devices but with different plunger assemblies only. This may further help minimizing manufacturing costs because different types of devices may be manufactured using the same standard parts and those standard parts may be pre-manufactured at relatively high volumes and low costs.

The piston 121 in the example is generally bell shaped and preferably oversized relative to walls of the cartridge 111 which form the chamber 118 and receive the piston 121. Thus the piston 121 and the cartridge 111 may be press fitted with one another. An elastic pretension due to the bell shape of the piston 121 preferably further provides for retention against rotation of the piston 121 and the cartridge 111 relative to each other. The chamber 118 may be predominantly sealed by a seal formed between the plunger 122 and the cartridge 111. In contrast the piston 121 may just seal the partition 118a of the chamber 118 sufficiently to hinder the dental substance in partition 118a to flow toward the partition 118b. The device 110 may be adapted such that the torque required for rotating the plunger 122 and the piston 121 relative to each other is lower that the torque which would be needed to rotate the piston 121 and the cartridge 111 relative to each other.

The device 110 further comprises a ratchet (not shown in detail) between the plunger 122 and the cartridge 111. The ratchet preferably provides for an audible click at certain rotational positions during a rotation of the plunger 122. Therefore the ratchet may enable audible metering of the dispensed amount of dental substance. Further the ratchet preferably permits free rotation of the plunger 122 for dispensing the dental substance and limited rotation in the opposite direction for releasing the dental substance from pressure built up during dispensation as outlined in other examples herein.

Figure 10:
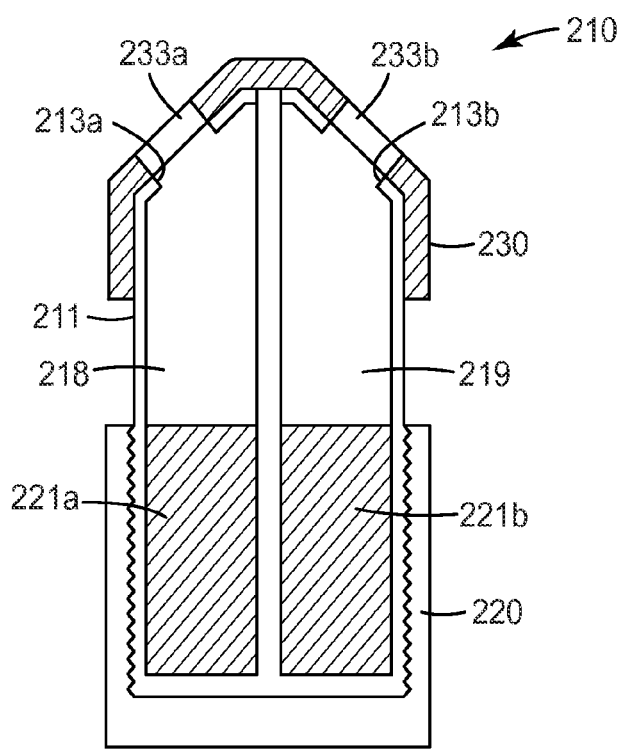
FIG. 10 is a cross-sectional view of a device according to still a further embodiment of the invention.

FIG. 10 shows a device 210 for containing two dental substances. The device 210 therefore has two chambers 218, 219 arranged side by side. In the example shown a plunger 220 has an inner thread for engaging with an outer thread provided at the cartridge 211. Thus a rotation of the plunger 220 and the cartridge 211 relative to each other preferably causes the plunger 220 and the cartridge 211 to telescopically move into each other. This preferably further causes pistons 221a and 221b received in the chambers 218, 219 to be moved into the chambers 218, 219, respectively, for dispensing the dental substances from dispensing openings 213a, 213b in the cartridge 211. Further the device 210 has a closure 230 having two openings 233a, 233b for openably closing the dispensing openings 213a, 213b in the cartridge 211. The closure 230 and the cartridge 211 are preferably otherwise at least functionally identical to the closure of certain other examples disclosed herein except that the closure 230 allows for dispensation and cutting of two dental substances.

Figure 11:
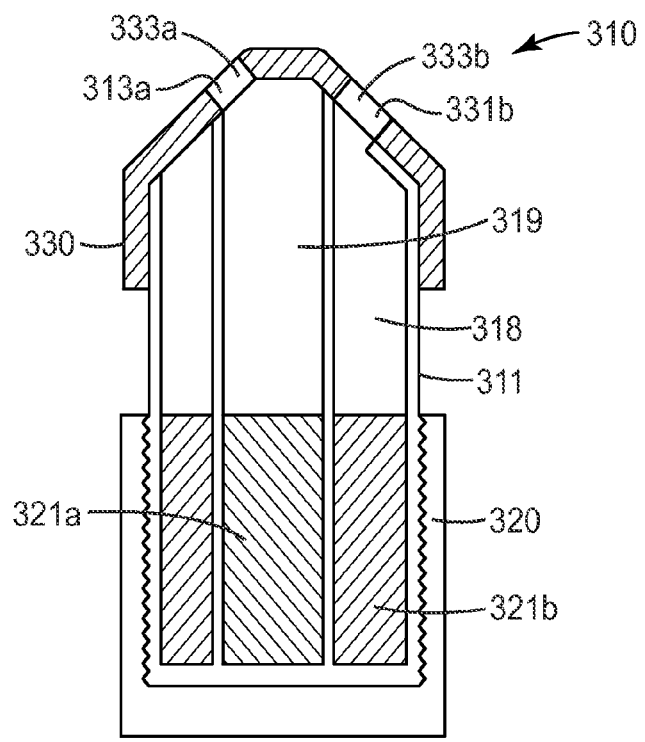
FIG. 11 is a cross-sectional view of a device according to a further embodiment of the invention.

FIG. 11 shows an alternative two-component device 310 having concentric chambers 318, 319 and respective dispensing openings 313a, 313b. Accordingly the device 310 has a closure 330 with openings 333a, 333b for openably closing the dispensing openings 313a, 313b and for cutting portions of the components dispensed. Again a cartridge 311 and a plunger 320 are screwed with one another via an outer thread at the cartridge 311 engaging an inner thread in the plunger 320. Pistons 321a, 321b are received within the chambers 319, 318 respectively and preferably move as the plunger 320 and the cartridge 311 are rotated relative to each other.

Figure 12:
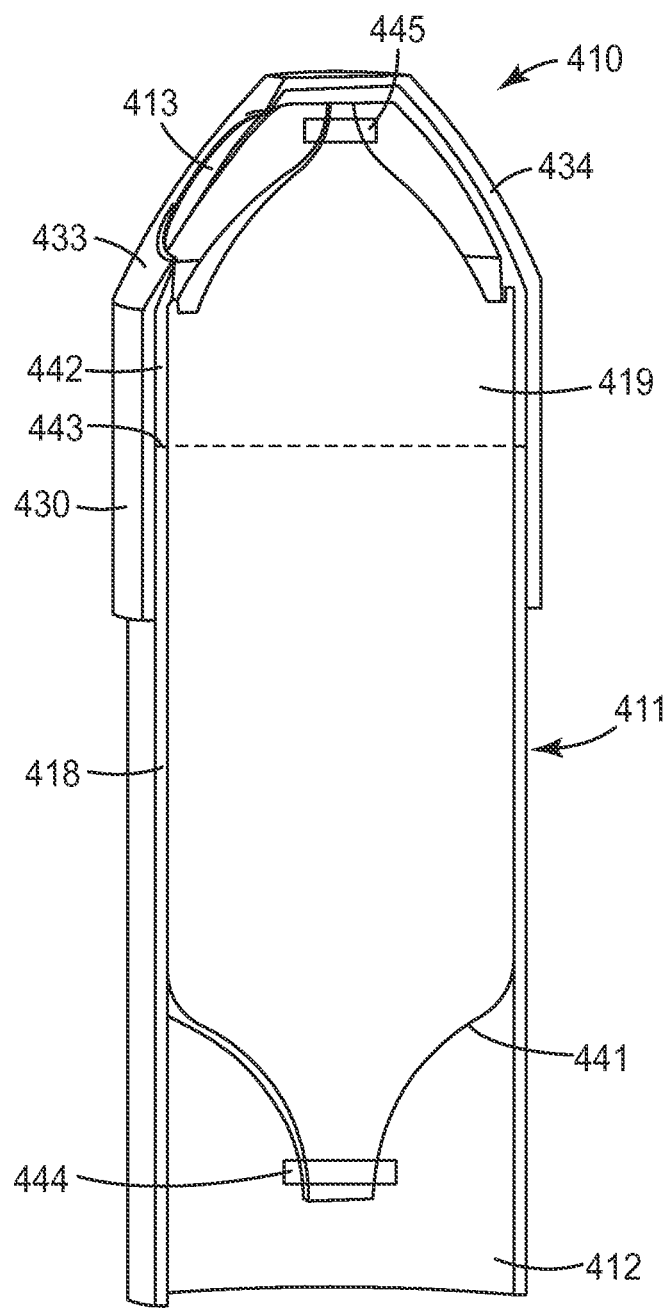
FIG. 12 is a perspective cross-sectional view of a device according to still a further embodiment of the invention.

FIG. 12 shows a device 410 which has a cartridge 411 which has a cartridge body 418 and a cartridge insert 419. The cartridge insert 419 in the example has a foil bag 441 which is attached with a hood 442. In conformity with other embodiments described herein the cartridge 411 has a cartridge opening 412 and a dispensing opening 413. The cartridge opening is formed within the cartridge body 418. The cartridge body 418 further has a fill opening 443 through which the cartridge insert 419 preferably can be inserted. In the example the cartridge body forms a generally cylindrical tube forming the cartridge opening 412 and the fill opening 443. The dispensing opening is formed within the hood 442.

The cartridge insert 419 is removably received within the cartridge body 418 so that, for example, the cartridge insert 419 can be replaced by another cartridge insert. For example an empty cartridge insert may be replaceable by a new one.

The foil bag 441 may be closed, for example by a closure clip 444 at a first end and may be received in the hood 442 at an opposite second end. The second end of the foil bag 441 may itself be open but the open end may be covered by the hood 442. Alternatively the second end of the foil bag may itself be closed, for example by a further clip 445. The foil bag may be attached with the hood 442 by an adhesive. For example the adhesive may bond an outer surface of the foil bag 441 circumferentially to an inner surface of the hood 442.

Thus the adhesive preferably further provides for a seal between the foil bag 441 and the hood 442. In case the foil bag 441 is itself closed at the second end the foil bag 441 may be opened for example by punching a knife or needle through the dispensing opening 413 into the foil bag 441. Thus a dental substance stored in the foil bag 441 may be dispensed through a hole punched through the foil and through the dispensing opening 413. The foil bag 441 may further be closed at the second end by a clip which is slidably attached to the foil bag 441. Therefore a pressure built up within the foil bag 441 for dispensing dental substance preferably causes the foil to slip out of the clip so that the foil bag 441 automatically opens upon pressurizing the foil bag 441. Thus the foil bag may be provided a self-opening closure clip.

A plunger (not shown) may be received within the cartridge opening 412. The plunger is preferably operable such that it compresses the foil bag 441 in a direction toward the dispensing opening 413 and thereby causes the dental substance to be urged toward the dispensing opening 412. Such a plunger may generally correspond to a plunger as shown in FIGS. 1 and 2, for example. However a plunger assembly as shown in FIGS. 7 and 8 may also be used. In this case the foil bag 441 may not be firmly filled and may be deformable around a spindle of such plunger assembly.

In the example the hood 413 carries a closure 430 which has an orifice 433. The closure 430 is adapted to openably close the dispensing opening 413. The closure 430 may be fixed at the cartridge insert 419, in particular at the hood 442, against detachment but is preferably rotatable relative to the hood 442. In a situation in which the closure 430 and the cartridge insert 419 are mated the closure 430 and the hood 442 are preferably rotatable relative to each other between an open position and a closed position. In the open position the orifice 433 may at least partially overlap the dispensing opening 413. Thus an outlet for the dental substance may be formed. In the closed position the dispensing opening 413 may be covered, preferably entirely covered, by a wall 434 of the closure 430. Further in the closed position the orifice 433 may also be covered, preferably entirely covered, by the hood 442.

Figure 13:
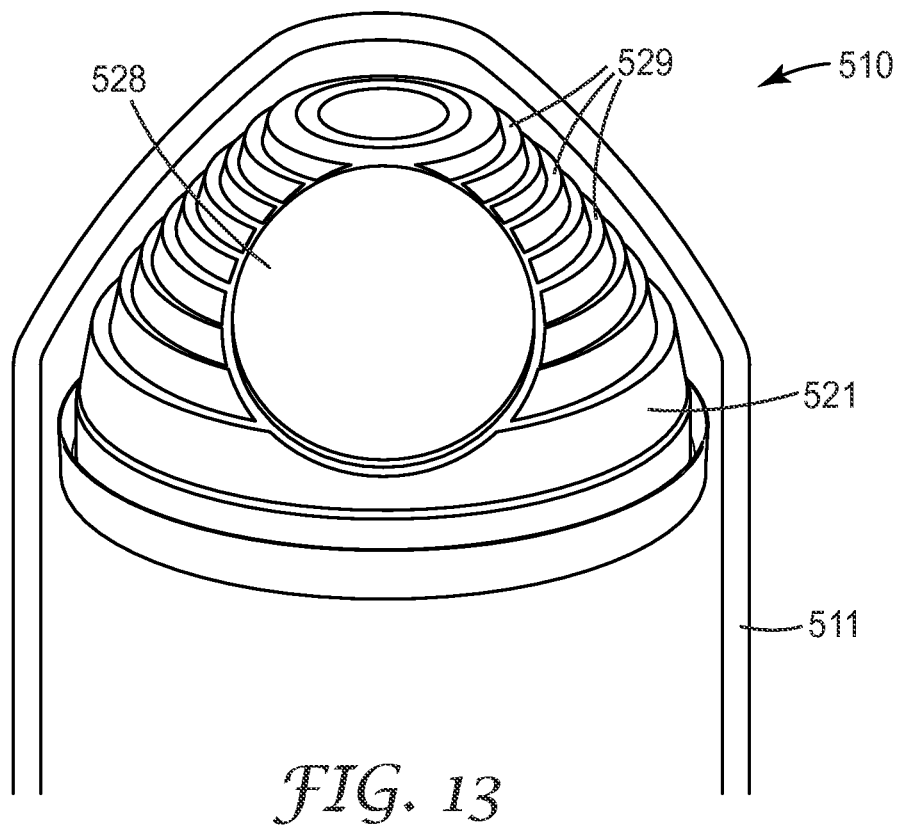
FIG. 13 is a partial perspective view of a device according to a further embodiment of the invention.

FIG. 13 shows a device 510 with a piston 521 and a cartridge 511. The device 510 comprises an "empty" indicator which is formed by a structured piston front face in combination with a transparent or translucent cartridge end wall that forms at least part of the cartridge front end. In this regard the piston front face corresponds to a face of the piston which faces a dispensing opening (not visible in this view) of the cartridge 511, and the front end of the cartridge 511 is the end which comprises the dispensing opening. In particular the piston 521 may be located in a non-empty position in which a dental substance is arranged between the piston front face and the cartridge end wall, and in an empty position in which the piston 521 touches the cartridge front end. In the example the piston 521 has circumferential fins 529 which in the empty position touch the transparent or translucent cartridge front wall. Due to the fins 529 touching the cartridge end wall in the empty position the fins are preferably visible through the cartridge end wall, thus indicating that substantially no dental substance is available within the device. The skilled person will recognize that the piston 521 may not directly touch the surface of the cartridge front wall but that a film or layer of dental substance may be arranged between the piston 521 (the fins 529) and the cartridge front wall. However the film of dental substance between the fins 529 and the cartridge front wall may be relatively thin and thus translucent so that the fins 529 are visible through cartridge front wall. Further between the fins 529 and the cartridge front wall the film of dental substance may be much thinner than the film of dental substance outside the fins 529 so that the fins 529 are preferably more clearly visible through cartridge front wall than the remainder of the piston 521. Thus even independent of any color of the piston and the dental substance (for example in case the dental substance and the piston are generally colorless and transparent) the variance in the film thickness of the dental substance preferably provides for a visible optical structure which can be recognized through the cartridge end wall. Accordingly the structured piston front face provides a visible marking at the cartridge front wall, and therefore a clear indication of the device being empty or substantially empty. This effect may be maximized by providing the piston 521 and the dental substance with different colors. This may enable the fins 529 to become clearly visible by their color relative to the color of the dental substance adjacent the fins 529.

The skilled person will further recognize that other structures than fins may be used to provide an empty indicator. In one example one or more raised elements in the form of a tip, ridge, dome or combination thereof may be provided. In a further example one or more raised characters may be used, for example characters which provide a marking "EMPTY" as the characters approach the cartridge end wall. In another example a wiper which basically extends radially over the piston face is provided. Such a wiper may be used in embodiments in which the piston or plunger rotates relative to the cartridge so that the wiper wipes an area of the cartridge end wall clean or generally clean from dental substance as it approaches the cartridge end wall. In the embodiments mentioned generally a clear indication of the device being empty may be provided to a user. A user therefore may not try to dispense further dental substance from an empty device. This may generally facilitate the use of the device 510.

The piston 521 further has a protrusion 528 which is adapted to fit within the dispensing opening of the cartridge in the empty position. The protrusion may be elastic or elastically suspended such that it snaps into the dispensing opening of the cartridge in the empty position. Thus the empty position may be clearly indicated to a user after dental substance is cut from the opening. This is because cutting of the dental material may cause dental substance to be wiped off from the protrusion so that the protrusion becomes clearly visible, for example through a transparent or translucent closure of the device. Further such protrusion may provide an audible indication (as it snaps into the dispensing opening) so that a user is additionally audibly provided with the indication that the device is empty.

Figure 14:
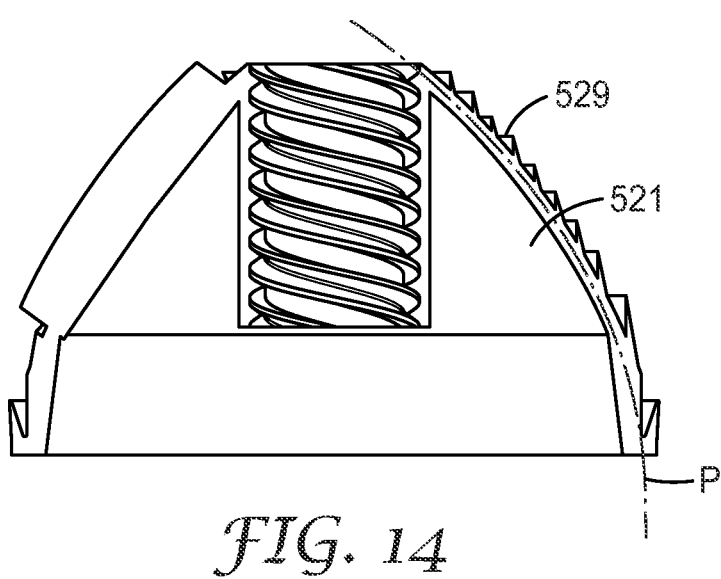
FIG. 14 is a cross-sectional view of a piston of the device shown in FIG. 13.

FIG. 14 illustrates the fins 529 of the piston 521 in a cross-sectional view. The profile of the piston face is generally sawtooth shaped with the individual teeth being inclined relative to an overall base profile P of the piston face. In the example the base profile P of the piston 529 is generally curved and the fins 529 protrude in a direction which is inclined relative to that curve by an angle which is less than 90°. The profile of the fins 529 may for example generally resemble a shark fin. Therefore in a situation in which the fins 529 are urged toward the cartridge end wall (not shown in this Figure) the fins 529 preferably bend into a predetermined direction toward conforming the basic profile P. Thereby the fins preferably displace dental substance between the fins and the remainder of the piston surface toward the ridge of the fins 529 so that the material displaced is made available for dispensing. It has been found that a piston having fins as illustrated provide for minimized residual dental substance between the piston and the cartridge end wall in the empty position of the piston relative to a piston having a flat surface without structures like fins.

In a further example (not illustrated) the piston end face may form part of a flexible membrane. In such an embodiment the piston may have a support body for supporting membrane for dispensing material from the device. However the membrane and the support body may be adapted such that the membrane can be pulled away from the support body, for example due to a contraction of the dental substance as a result of temperature change during storage of the device. Detailed embodiments of a piston with a membrane are disclosed in WO 2008/021732 which is incorporated by reference herein.

The skilled person will recognize that certain features of embodiments described herein may be used for other embodiments described or not described herein. For example each of the embodiments may have a ratchet which allows for audible metering of a dental substance dispensed and for limiting any operation of the device which would cause the dental substance to be retracted. Further each of the embodiments may have a closure allowing for cutting off a portion of a dental substance dispensed or multiple portions of multiple dental substances dispensed.

Figure 15:
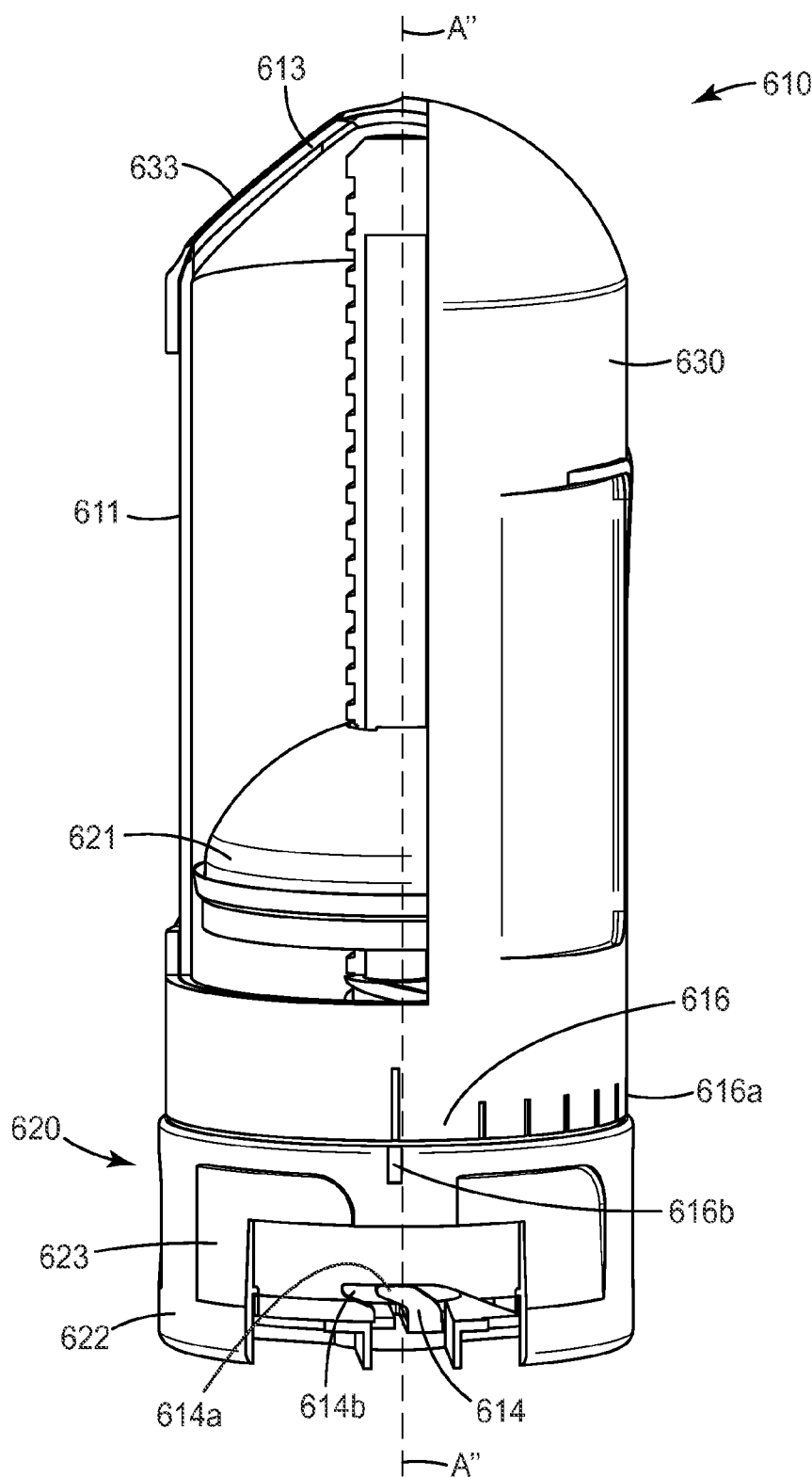
FIG. 15 is a partial cross-sectional view of a device according to a further embodiment of the invention.

FIG. 15 shows a device 610 in a partial cross-sectional view. The device 610 has a cartridge 611 which in this example forms an insert of a cup-shaped closure 630. The device further has a plunger assembly 620 which comprises a piston 621 and a plunger 622. The plunger 622 at its rear end forms a handle 623. In the example the closure 630 and the plunger 622 form a housing of the device which entirely encloses or surrounds the cartridge 611. Accordingly the outer shell of the device 610 may be essentially only formed by a part of the plunger 622 and the closure 630. Therefore a use of the device may be restricted to an operation of the closure 630 and the plunger 622 only. In particular a user can only operate the device by operating the plunger 622 and the closure 630 relative to each other. This helps maximizing the reliability in operation of the device 610. Although preferably the housing encloses the cartridge 611, for example generally entirely encapsulates the cartridge 611 from the environment to avoid dirt to penetrate between the cartridge 611 and the housing, the housing may alternatively surround the cartridge 611 but may have openings exposing the cartridge partially. A housing having openings may nevertheless form an outer shell by which the device 610 can be handled.

The principle operation of the device 611 generally corresponds to the operation of the device 110 illustrated in FIGS. 7 through 9. In particular the cartridge 611 has a dispensing opening 613. The plunger assembly 620 is received within the cartridge 611. In particular the plunger 622 extends with its front end into the cartridge 611 and is adapted to position the piston 621 within the cartridge 611. The closure 630 and the cartridge 611 are rotatable relative to each other. The closure 630 and the cartridge 611 can particularly be rotated between a closed position and an open position with one another. In the closed position the closure 630 covers, preferably entirely covers, the dispensing opening 613 of the cartridge 611, and in the open position an orifice 633 of the closure 630 overlaps at least partially, preferably entirely overlaps, with the dispensing opening 613. Accordingly the overlapping dispensing opening 613 and orifice 633 form an outlet of the device 610 in the open position. The outlet preferably allows a dental substance stored in the device 610 to be directly dispensed for use. The rotation of the closure 630 and the cartridge 611 relative to each other is preferably limited to an area between the open and the closed position and blocked outside. Stops (not shown) in the device 610 preferably provide for such limitation. Further the closure 630 also comprises a cutter in the form of a cutting edge at least partially forming the orifice 633. Thus the closure 630 allows a portion of the dental substance protruding from the dispensing opening 613 to be cut upon rotation of the closure 630 and the cartridge 611 from the open toward the closed position.

The piston 621 and the plunger 622 of the plunger assembly 620 together form a screw connection as explained above. Thus a rotation of the plunger 622 and the piston 621 relative to each other preferably causes the plunger 622 and the piston 621 to displace relative to each other in a dimension parallel to a longitudinal axis A". Because the piston 621 and the cartridge 611 are preferably retained against twisting relative to each other (preferably by friction) in the assembled device a rotation of the cartridge 611 and the plunger 622 relative to each other causes the piston 621 to urge dental substance contained within the cartridge 611 toward the dispensing opening 613.

The movement of the piston 621 for dispensing a portion of the dental substance is preferably caused by rotating the plunger 622 relative to the closure 630. Because the cartridge 611 and the closure 630 are anti-twist locked (in particular reverse twist lock) outside the area between the open and the closed position the device 610 is generally adapted such that a rotation of the plunger 622 and the closure 630 relative to each other eventually includes also a rotation of the cartridge 611 and the closure 630 relative to each other until the stop is reached and anti-twist locks the cartridge 611 and the closure 630 relative to each other. A further rotation of the plunger 622 and the closure 630 relative to each other then causes the cartridge 611 (anti-twist locked with the closure 630) and the plunger 622 to rotate relative to each other and cause the piston 621 to displace. Preferably the device 610 is adapted such that a rotation of the plunger 622 and the closure 630 relative to each other to dispense a portion of the dental material causes the cartridge 611 and the closure 630 to be urged toward the open position, and a reverse rotation of the plunger 622 and the closure 630 relative to each other causes the cartridge 611 and the closure 630 to be urged toward the closed position. Accordingly the device 610 implements an automatic opening mechanism which opens upon rotating the plunger 622 and the closure 630 relative to each other.

The device 610 further has a ratchet 614 between the plunger 622 and the cartridge 611. The ratchet 614 has a flexible or resilient pawl 614a arranged at the plunger 622 and at least one recess 614b arranged at the cartridge 611. The ratchet 614 preferably provides for an audible click at certain rotational positions during a rotation of the plunger 622 relative to the cartridge 611. Further the ratchet 614 forms a one-way clutch which enables a rotation of the plunger 622 and the cartridge 611 relative to each other in the dispensing direction but blocks a free rotation of the plunger 622 and the cartridge 611 relative to each other in the opposite backward direction. Accordingly the plunger 622 and the closure 630 (cartridge 611) rotated in the dispensing direction relative to each other preferably causes the device 610 to open and a portion of the dental substance to be dispensed from the orifice 633. The plunger 622 and the closure 630 (cartridge 611) rotated in the backward direction relative to each other preferably causes the device 610 to close and to release pressure inside the cartridge 611 eventually built up by the piston (not shown) as further explained in detail in the following.

The device 610 has further metering means 616 having a metering scale 616a and a metering pointer 616b. In the example the metering scale 616a is arranged on the outside of the closure 630 and the metering pointer 616b is arranged on the outside of the plunger 622, although the person skilled in the art will recognize that the metering scale may likewise be arranged on the plunger and the metering pointer may be arranged on the closure. Accordingly a portion of dental substance may be dispensed at a desired amount controllable by use of the metering means independent from the ratchet. Further the ratchet may be adapted to provide for anti-twist locking at a plurality positions with only providing for an audible click some of the plurality of positions but not in intermediate positions. For example the ratchet may provide for an audible click and reverse twist lock in main positions each representing the dispensation of a predetermined portion of dental substance, and substantially only a reverse twist lock in intermediate positions.

Figure 16A:
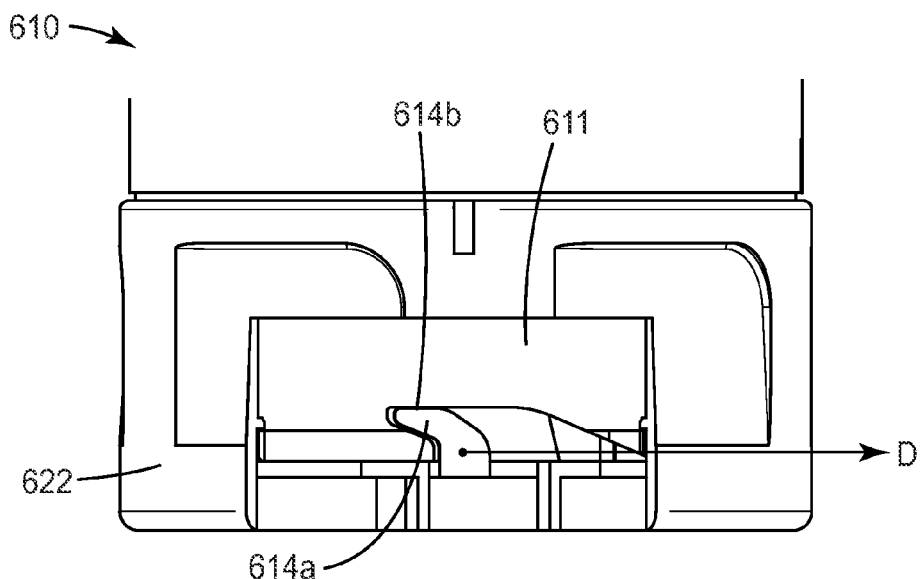
FIGS. 16a-16d are cross-sectional views illustrating an operation of a device according to an embodiment of the invention.

FIG. 16a shows a portion of the device 610 in an enlarged view. The plunger 622 is shown in a partial cross-sectional view with an imaginary cut-away providing view on a portion of the cartridge 611. In the situation shown the pawl 614a engages with the recess 614b. The recess 614b is arranged at a circumferential wall of the cartridge 611 and the pawl 614a is arranged at an appropriate position on the plunger 622 to engage with the recess 614b. The person skilled in the art will recognize that instead of a recess other means may be used such as a detent protruding from a rear end face of the cartridge 611, or a combination thereof.

Figure 16B:
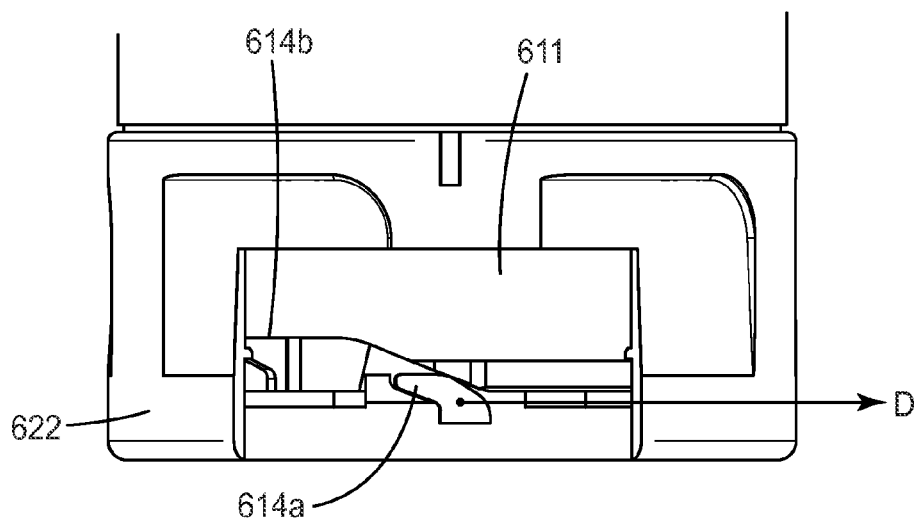
Figure 16C:
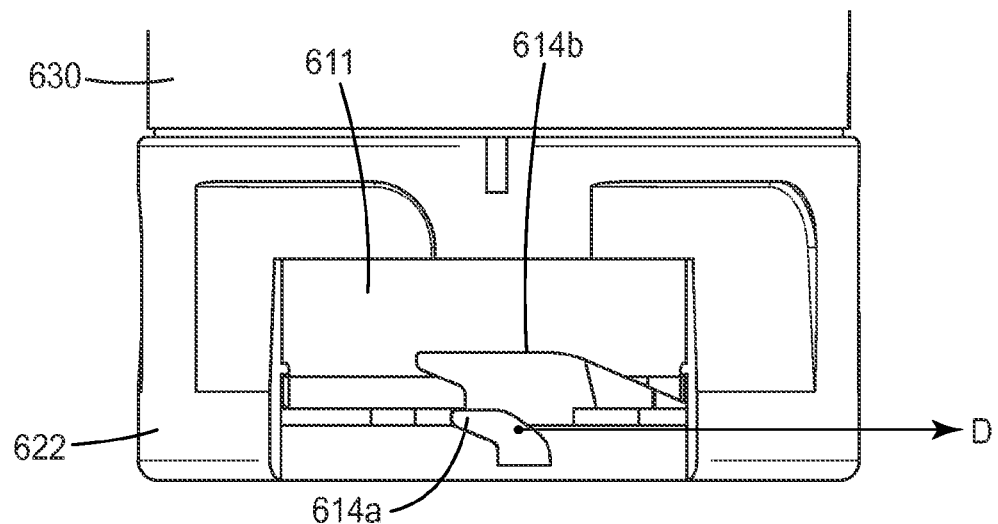

The plunger 622 rotated toward the dispensing direction D results in the situation illustrated in FIG. 16b. As shown the pawl 614a has reached an end of the recess 614b and further rotation of the plunger 622 toward the dispensing direction D causes the pawl 614a to be bent down or compressed by the cartridge 611. Even further rotation of the plunger 622 toward the dispensing direction D results in the situation illustrated in FIG. 16c. In this situation the pawl 614a is urged down by the cartridge, but a slight further rotation in the direction of D as shown in FIG. 16d causes the pawl 614a to snap into the recess 614b, thereby causing an audible click.

The movement of the plunger 622 relative to the cartridge 611 as illustrated in FIGS. 16a to 16d may cause a predetermined amount of dental substance to be dispensed. Further during this movement preferably the closure 630 and the cartridge 611 are positioned to the open position. Each further movement to further positions causing subsequent clicks preferably causes the dispensation of proportional additional portions of dental substance.

Figure 16D:
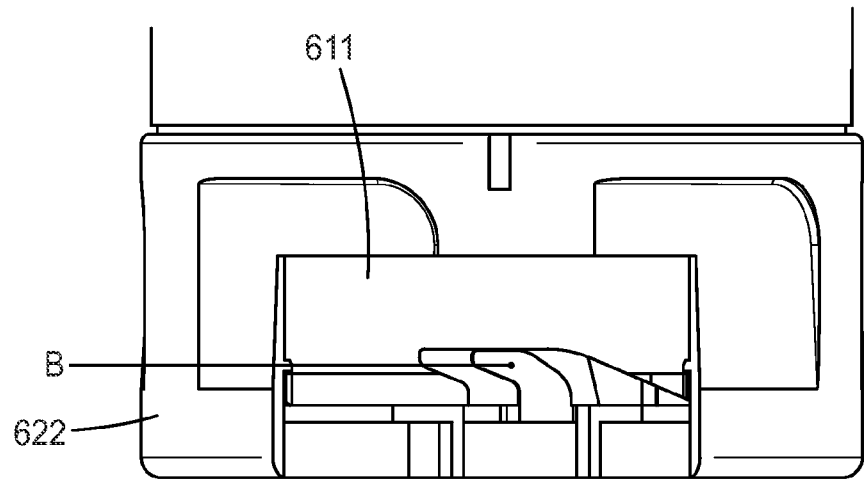

In the situation shown in FIG. 16d the plunger 622 may be rotated reversely or backwards in the direction of B which causes the pawl 614a and the recess 614b to engage with each other as shown in FIG. 16a. During the rotation backwards the cartridge 611 and the closure 630 preferably get positioned in the closed position. Further due to the relative rotation between the cartridge 611 and the plunger 622 the piston (not shown) is preferably slightly retracted within the cartridge and thus pressure built up by the piston to dispense the dental substance is preferably relieved. Thus, during storage of the used device 610 dental substance may be prevented from flowing between the closure 630 and the cartridge 611 over time.

Figure 17A:
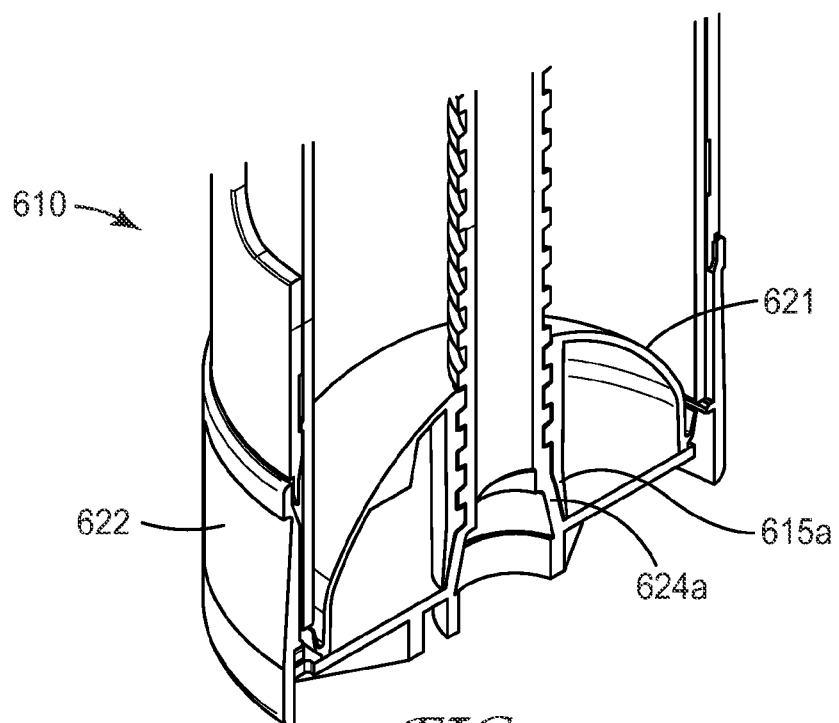
FIGS. 17a, 17b are cross-sectional views illustrating further details of a device according to an embodiment of the invention.

FIG. 17a illustrates in a cross-sectional view the device 610 with the plunger assembly 620 in a storage position. The storage position corresponds to a position of a new unused device. The piston 621 has an inner thread 615 extending through the piston 621 and engaging with a spindle 624 of the plunger 622. On a rear face of the piston which is facing the rear end of the plunger 622 the piston 621 has a seal 615a which extends circumferentially around the opening formed by the inner thread 615. In the storage position the seal 615a abuts at the plunger 622, in particular a sealing cone 624a at the spindle 624 of the plunger, so that the opening in the piston 621 formed by the inner thread 615 is sealed by the plunger 622. This allows a relatively good encapsulation of the dental substance in the unused device during storage over a longer time (for example several months or years), and further allows a certain play between the inner thread of the piston and the outer thread of the spindle 624. Latter further helps minimizing the force required to rotate the piston 621 and the spindle 624 relative to each other.

Figure 17B:
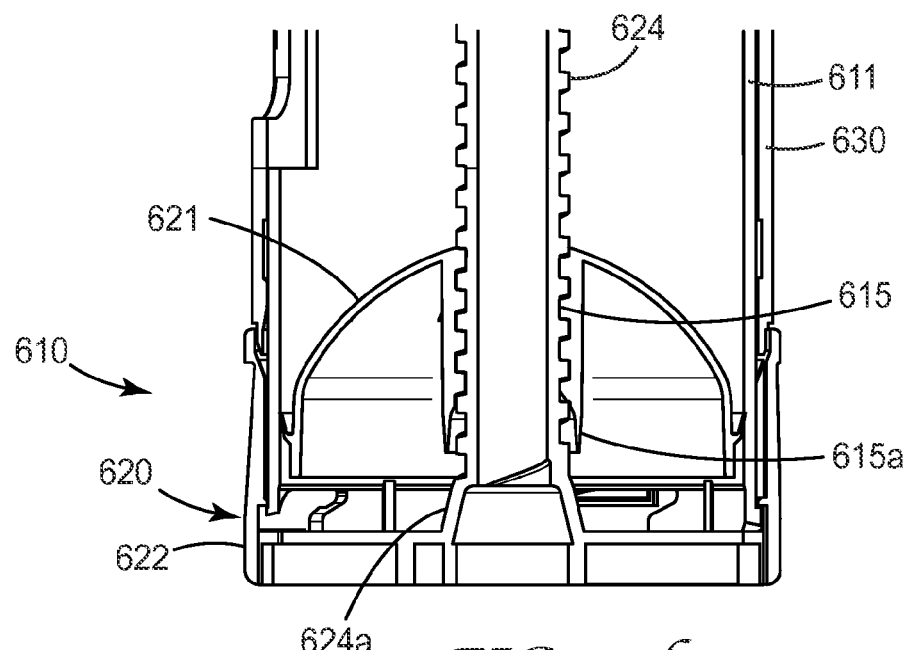

FIG. 17b shows the piston 621 positioned away from the storage position, for example in consequence of a dispensation of a portion of dental substance. The seal 615a is placed away from the sealing cone 624a of the plunger 622. Thus a space is present between the seal 615a and the sealing cone 624a which avoids any friction between the seal 615a and the sealing cone 624a during operation of the device.

The invention claimed is:

1. A device for dispensing a dental substance, the device comprising:
   a cartridge for containing the dental substance and a plunger, the cartridge comprising a dispensing opening,
   a screw mechanism which is operable to urge the dental substance toward the dispensing opening of the cartridge,
   a closure being adapted to openably close the dispensing opening, wherein the closure comprises a cutter for cutting off a portion of the dental substance which protrudes over the dispensing opening, wherein the closure has a closure wall through which an orifice extends, the closure and the cartridge being movable relative to each other between a closed position in which the closure wall covers the dispensing opening and an open position in which the dispensing opening and the orifice overlap at least partially, and
   the device being adapted to provide an indication of a predetermined amount of dental substance being dispensed,
   wherein the indication comprises an audible click provided by a ratchet permitting relative rotation of the plunger and the cartridge in a dispensing direction and restricting rotation in the opposite direction, wherein the ratchet comprises a pawl and a complementary groove, wherein the pawl cooperates with the complementary groove to enable rotation in the opposite direction of the dispensing direction, while the pawl and the complementary groove are engaged, over a predetermined distance, to cause the closure and the cartridge to move relative to each other to the closed position.

2. The device of claim 1, wherein the closure forms or comprises a handle by which the closure can be held and operated by a user of the device.

3. The device of claim 1, wherein the dispensing opening and the orifice have generally circular cross-sections of generally equal diameters.

4. The device of claim 1, wherein the closure forms a slide valve or a rotary slide valve.

5. The device of claim 1, comprising at least a component of a type 0 dental impression material.

6. The device of claim 1, wherein the plunger is threaded and forms part of the screw mechanism.

7. The device of claim 1, wherein the cartridge is adapted for containing two dental substances separate from each other, the cartridge further having a further dispensing opening, and wherein the closure has a further orifice for opening the further dispensing opening in the open position of the closure.

8. The device of claim 1, wherein the pawl of the ratchet cooperates with the complementary groove to enable the rotation in the opposite direction of the dispensing direction to a position where the pawl and the groove are interlocked and further rotation in the opposite direction is restricted.

9. The device of claim 1, wherein the pawl of the ratchet has a general L-shaped structure, and wherein the complementary groove has a complementary L-shaped structure.

10. The device of claim 1, wherein the closure wall forms a circumferential cutting edge delimiting the orifice.

11. The device of claim 10, wherein the cartridge has an outward convex cartridge end face through which the dispensing opening extends, the cartridge end face generally corresponds in shape to a portion of an imaginary sphere, and wherein the cutting edge extends along a line on the same imaginary sphere.

12. A device for dispensing a dental substance, the device comprising:
a cartridge for containing the dental substance and a plunger, the cartridge comprising a dispensing opening,
a screw mechanism which is operable to urge the dental substance toward the dispensing opening of the cartridge,
a closure being adapted to openably close the dispensing opening, wherein the closure comprises a cutter for cutting off a portion of the dental substance which protrudes over the dispensing opening, wherein the closure has a closure wall through which an orifice extends, the closure and the cartridge being movable relative to each other between a closed position in which the closure wall covers the dispensing opening and an open position in which the dispensing opening and the orifice overlap at least partially, and
the device being adapted to provide an indication of a predetermined amount of dental substance being dispensed,
wherein the indication comprises an audible click provided by a ratchet permitting relative rotation of the plunger and the cartridge in a dispensing direction and restricting rotation in the opposite direction, wherein the ratchet comprises a pawl and a complementary groove, wherein the pawl and the complementary groove cooperate such that at the point when the pawl enters into the complementary groove, a predetermined amount of rotation in the opposite direction is allowed to enable rotation in the opposite direction of the dispensing direction over a predetermined distance.

13. The device of claim 12, wherein the rotation in the opposite direction of the dispensing direction over the predetermined distance causes the closure and the cartridge to move relative to each other to the closed position.

14. The device of claim 12, wherein the pawl of the ratchet cooperates with the complementary groove to enable the rotation in the opposite direction of the dispensing direction over the predetermined distance to a position where the pawl and the groove are interlocked and further rotation in the opposite direction is restricted.

15. The device of claim 12, wherein the pawl of the ratchet has a general L-shaped structure, and wherein the complementary groove has a complementary L-shaped structure.

16. The device of claim 12, wherein the closure forms or comprises a handle by which the closure can be held and operated by a user of the device.

17. The device of claim 12, wherein the closure wall forms a circumferential cutting edge delimiting the orifice.

18. The device of claim 12, wherein the dispensing opening and the orifice have generally circular cross-sections of generally equal diameters.

19. The device of claim 12, wherein the closure forms a slide valve or a rotary slide valve.

20. The device of claim 12, wherein the plunger is threaded and forms part of the screw mechanism.

* * * * *